(12) United States Patent
Sutton et al.

(10) Patent No.: US 11,241,163 B2
(45) Date of Patent: Feb. 8, 2022

(54) MEASURING BLOOD VESSEL CHARACTERISTICS WITH MRI

(71) Applicant: THE BOARD OF TRUSTEES OF THE UNIVERSITY OF ILLINOIS, Urbana, IL (US)

(72) Inventors: Bradley P. Sutton, Savoy, IL (US); Alexander M. Cerjanic, Champaign, IL (US); Luisa Ciobanu, Gif-sur-Yvette (FR); Denis LeBihan, Gif-sur-Yvette (FR); Jing-Rebecca Li, Palaiseau (FR); Gabrielle Fournet, Gif-sur-Yvette (FR)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 546 days.

(21) Appl. No.: 16/002,958

(22) Filed: Jun. 7, 2018

(65) Prior Publication Data
US 2018/0353099 A1    Dec. 13, 2018

Related U.S. Application Data

(60) Provisional application No. 62/516,958, filed on Jun. 8, 2017.

(51) Int. Cl.
*A61B 5/055* (2006.01)
*G06T 7/00* (2017.01)
(Continued)

(52) U.S. Cl.
CPC ............ *A61B 5/055* (2013.01); *A61B 5/0263* (2013.01); *A61B 5/4088* (2013.01);
(Continued)

(58) Field of Classification Search
CPC . A61B 2576/026; A61B 5/0263; A61B 5/055; A61B 5/4088; A61B 5/489;
(Continued)

(56) References Cited

U.S. PATENT DOCUMENTS 7,706,857 B2    4/2010    Aletras et al.
8,395,385 B2    3/2013    Lee et al.
(Continued)

OTHER PUBLICATIONS

Ahlgren, Andre et al., "Quantification of microcirculatory parameters by joint analysis of flow-compensated and non-flow-compensated intravoxel incoherent motion (IVIM) data", NMR Biomed. 2016; 29: 640-649, 2016, 10pgs.
(Continued)

*Primary Examiner* — Amelie R Davis
(74) *Attorney, Agent, or Firm* — Guntin & Gust, PLC; Matthew Tropper

(57) ABSTRACT

Aspects of the subject disclosure may include, for example, obtaining first magnetic resonance imaging (MRI) data of a subject, wherein the first MRI data is obtained during a first scan of a subject, wherein the first scan has a first diffusion sampling time, and wherein the first diffusion sampling time is selected in order to facilitate use of the first MRI data to determine a first Intravoxel Incoherent Motion (IVIM) effective diffusion coefficient in a Stationary Random Flow (SRF) regime; obtaining second MRI data of the subject, wherein the second MRI data is obtained during a second scan of the subject, wherein the second scan has a second diffusion sampling time, wherein the second diffusion sampling time is longer than the first diffusion sampling time, and wherein the second diffusion sampling time is selected in order to facilitate use of the second MRI data to determine a second IVIM effective diffusion coefficient in a pseudodiffusion regime; determining a blood velocity value based
(Continued)

upon the first MRI data; and determining a segment length value based upon the second MRI data. Additional embodiments are disclosed.

20 Claims, 16 Drawing Sheets

(51) Int. Cl.
  *A61B 5/026*  (2006.01)
  *G01R 33/563*  (2006.01)
  *A61B 5/00*  (2006.01)

(52) U.S. Cl.
  CPC ...... *G01R 33/56341* (2013.01); *G06T 7/0012* (2013.01); *A61B 5/489* (2013.01); *A61B 2576/026* (2013.01); *G01R 33/56366* (2013.01); *G06T 2207/10016* (2013.01); *G06T 2207/10088* (2013.01); *G06T 2207/20104* (2013.01); *G06T 2207/30101* (2013.01)

(58) Field of Classification Search
  CPC ........ G01R 33/56341; G01R 33/56366; G06T 2207/10016; G06T 2207/10088; G06T 2207/20104; G06T 2207/30101; G06T 7/0012
  See application file for complete search history.

(56) References Cited

U.S. PATENT DOCUMENTS

| | | | |
|---|---|---|---|
| 8,395,386 | B2 | 3/2013 | Kimura et al. |
| 2015/0168527 | A1* | 6/2015 | Topgaard .............. A61B 5/7207 600/419 |
| 2017/0024886 | A1* | 1/2017 | Dickrell, III ........... A61B 5/026 |
| 2017/0234956 | A1* | 8/2017 | Feiweier .......... G01R 33/56341 324/309 |
| 2018/0224514 | A1 | 8/2018 | Topgaard et al. |

OTHER PUBLICATIONS

Baloyannis, Stavros J. et al., "The vascular factor in Alzheimer's disease: A study in Golgi technique and electron microscopy", Journal of the Neurological Sciences 322 (2012) 117-121, 2012, 5 pages.

Bell, Mary A. et al., "Morphometric Comparison of Hippocampal Microvasculature in Ageing and Demented People: Diameters and Densities", Acta Neuropathol (Berl)(1981) 53:299-318, 1981, 20 pages.

Buchweitz-Milton, Ellen et al., "Perfused Capillary Morphometry in the Senescent Brain", Neurobiology of Aging, vol. 8, pp. 271-276. Pergamon Journals Ltd., 1987, 1987, 6 pages.

Buee, L. et al., "Pathological alterations of the cerebral microvasculature in Alzheimer's disease and related dementing disorders", Acta Neuropathol (1994) 87: 469-480, 1994, 12 pages.

Cerjanic, et al., "Using IVIM and diffusion weighted MRI to measure vascular properties in the aging brain", CRCNS 2015 Poster, Presented Sep. 28, 2015 through Sep. 30, 2015, Sep. 28, 2015, 1.

Cassot, Francis et al., "A Novel Three-Dimensional Computer-Assisted Method for a Quantitative Study of Microvascular Networks of the Human Cerebral Cortex", Microcirculation, 13: 1-18, 2006, 2006, 18 pages.

Cohen, Alexander D. et al., "The effect of low b-values on the intravoxel incoherent motion (IVIM) derived pseudodiffusion parameter in liver", Magn Reson Med. Author manuscript; available in PMC Jul. 29, 2015., Jul. 29, 2015, 12 pages.

Dixon, W. T., "Separation of Diffusion and Perfusion in Intravozel Incoherent Motion MR Imaging: A Modest Proposal with Tremendous Potential", Radiology 1988; 168:566-567, 1988, 2 pages.

Drachman, David A., "The amyloid hypothesis, time to move on: Amyloid is the downstream result, not cause, of Alzheimer's disease", Alzheimer's & Dementia 10 (2014) 372-380, 2014, 9 pages.

Fessler, Jeffrey A. et al., "Nonuniform Fast Fourier Transforms Using Min-Max Interpolation", IEEE Transactions on Signal Processing, vol. 51, No. 2, Feb. 2003, Feb. 2003, 15 pages.

Fournet, Gabrielle et al., "Euromar 2017 Abstract", p. 369, 2017.

Fournet, Gabrielle, "IVIM", IVIM : modélisation, validation expérimentale et application à des modèles animaux. Medical Physics [physics.med-ph]. Université Paris-Saclay, 2016. English., 2016, 190 pages.

Gauthier, Serge et al., "Why has therapy development for dementia failed in the last two decades?", Alzheimer's & Dementia 12 (2016) 60-64, 2016, 5 pages.

Gudbjartsson, Hakon et al., "The Rician Distribution of Noisy MRI Data", MRM 34.910-914 (1995), 1995, 5 pages.

Hansen, Michael S. et al., "Gadgetron: An Open Source Framework for Medical Image Reconstruction", Magnetic Resonance in Medicine 69:1768-1776 (2013), 2013, 9 pages.

Henkelman, R. M. et al., "A Quantitative Interpretation of IVIM Measurements of Vascular Perfusion in the Rat Brain", MRM 32464-469 (1994), 1994, 6 pages.

Hill, Mark D., "Amdahl's Law in the Multicore Era", 2008 IEEE; http://www.cs.wisc.edu/~markhill/, 2008, 1 page.

Holtrop, Joseph L. et al., "High spatial resolution diffusion weighted imaging on clinical 3 T MRI scanners using multislab spiral acquisitions", J. Med. Imag. 3(2), 023501 (2016), MedicalImaging.SPIEDigitallibrary.org, 2016, 8 pages.

Hudetz, Antal G. et al., "Heterogeneous Autoregulation of Cerebrocortical Capillary Flow: Evidence for Functional Thoroughfare Channels?", Microvascular Research 51, 131-136 (1996); Article No. 0015, 1996, 6 pages.

Hwu, Wen-Mei W. et al., "Accelerating MR Image Reconstruction on GPUs", 2009 IEEE; ISBI 2009, 2009, 4 pages.

Inati, Souheil J. et al., "ISMRM Raw Data Format: A Proposed Standard for MRI Raw Datasets", Magnetic Resonance in Medicine 77:411-421 (2017), Jan. 29, 2016, 11 pages.

James, Bryan D. et al., "Contribution of Alzheimer disease to mortality in the United States", 2014 American Academy of Neurology, Mar. 25, 2014, 6 page.

Kennan, Richard P. et al., "A General Model of Microcirculatory Blood Flow Effects in Gradient Sensitized MRI", Med. Phys. 21 (4), Apr. 1994, 8 pages.

Kim, Jeongtae et al., "Penalized maximum likelihood estimation of lifetime and amplitude images from multi-exponentially decaying fluorescence signals", 2013 OSA Aug. 26, 2013 | vol. 21, No. 17, Aug. 21, 2013, 14 pages.

Lauwers, Frederic et al., "Morphometry of the human cerebral cortex microcirculation: General characteristics and space-related profiles", NeuroImage 39 (2008) 936-948, www.elsevier.com/locate/ynimg, Sep. 21, 2007, 13 pages.

Le Bihan, Denis, "Magnetic Resonance Imaging of Perfusion", Magnetic Resonance in Medicine 14,283-292 (1990), 1990, 10pgs.

Le Bihan, Denis et al., "MR Imaging of Intravoxel Incoherent Motions: Application to Diffusion and Perfusion in Neurologic Disorders", Radiology 1986; 161:401-407, 1986, 7 pages.

Le Bihan, Denis et al., "Separation of Diffusion and Perfusion in Intravoxel Incoherent Motion MR Imaging", Radiology 1988; IMI:497-505, 1988, 9 Pages.

Le Bihan, Denis et al., "The Capillary Network: A Link between IVIM and Classical Perfusion", Magnetic Resonance in Medicine 27, 171-178 (1992), 1992, 8 pages.

Le Bihan, Denis, "What can we see with IVIM MRI?", NeuroImage 187 (2019) 56-67, https://doi.org/10.1016/j.neuroimage.2017.12.062; Received in revised form 28, Available online Dec. 22, 2017; p. 56-67, Dec. 22, 2017, 12pgs.

Lehmann, Manja et al., "A novel use of arterial spin labelling MRI to demonstrate focal hypoperfusion in individuals with posterior cortical atrophy: a multimodal imaging study", J Neurol Neurosurg Psychiatry Month 2016 vol. 0 No. 0, JNNP Online First, published on Jan. 5, 2016 as 10.1136/jnnp-2015-312782, Jan. 5, 2016, 3 pages.

(56) References Cited

OTHER PUBLICATIONS

Liu, Ying et al., "Different post label delay cerebral blood flow measurements in patients with Alzheimer's disease using 3D arterial spin labeling", Magnetic Resonance Imaging 33 (2015) 1019-1025, 2015, 7 pages.
Lokkegaard, Annemette et al., "Stereological Estimates of Number and Length of Capillaries in Subdivisions of the Human Hippocampal Region", HIPPOCAMPUS 11:726-740 (2001), Jan. 15, 2001, 15 Pages.
Mattiello, James et al., "The b Matrix in Diffusion Tensor Echo-Planar Imaging", MRM 37:292-300 (1997), 1997, 9 pages.
Meier-Ruge, W. et al., "Stereological Changes in the Capillary Network and Nerve Cells of the Aging Human Brain*", Mechanisms of Ageing and Development, 14 (1980) 233-243, 1980, 11 pages.
Merboldt, Klaus-Dietmar et al., "Diffusion Imaging of the Human Brain in Vivo Using High-Speed Steam MRI", Magnetic Resonance in Medicine 23, 179-192, 1992, 14 pages.
Moody, Dixon M. et al., "Microvascular changes in the white mater in dementia", J Neurol Sci. Aug. 15, 2009; 283(1-2): 28-31, NIH Public Access, Aug. 15, 2009, 11 pages.
Neil, Jeffrey J. et al., "An Evaluation of the Sensitivity of the Intravoxel Incoherent Motion (IVIM) Method of Blood Flow Measurement to Changes in Cerebral Blood Flow", MAiM 32:60-65 (1994), 1994, 6 pages.
Neil, Jeffrey J. et al., "Detection of Pseudodiffusion in Rat Brain following Blood Substitution with Perfluorocarbon", Journal of Magnetic Resonance 97, 194-20 1 (1992), Oct. 7, 1991, 8 pages.
Niwa, Kiyoshi et al., "Ab1-40-related reduction in functional hyperemia in mouse neocortex during somatosensory activation", PNAS, Aug. 15, 2000, vol. 97, No. 17, pp. 975-9740, Aug. 15, 2000, 6 pages.
Orton, Matthew R. et al., "Improved Intravoxel Incoherent Motion Analysis of Diffusion Weighted Imaging by Data Driven Bayesian Modeling", Magnetic Resonance in Medicine 71:411-420 (2014), wileyonlinelibrary.com, Feb. 13, 2013, 10 pages.
Poot, D. H. et al., "Bias correction of maximum likelihood estimation in quantitative MRI", https://www.spiedigitallibrary.org/conference-proceedings-of-spie, Mar. 13, 2013, 7 pages.
Prince, Martin et al., "The Global Impact of Dementia an Analysis of Prevalence, Incidence, Cost and Trends", Alzheimer's Disease International (ADI), London., Aug. 2015, 87 pages.
Puls, Imke et al., "Diagnostic Impact of Cerebral Transit Time in the Identification of Microangiopathy in Dementia", http://stroke.ahajournals.org/, 1999, 6 pages.
Sanderson, Conrad, "Armadillo: An Open Source C++ Linear Algebra Library for Fast Prototyping and Computationally Intensive Experiments", Technical Report, NICTA, 2010, Sep. 2010, 16 pages.
Shao, Wei-Hua et al., "Stereological Investigation of Age-Related Changes of the Capillaries in White Matter", The Anatomical Record 293:1400-1407 (2010), 2010, 8 pages.
Sorensen, Thomas S. et al., "Accelerating the Nonequispaced Fast Fourier Transform on Commodity Graphics Hardware", IEEE Transactions on Medical Imaging, vol. 27, No. 4, Apr. 2008, Apr. 2008, 10 pages.
Stark, Henry et al., "Probability, Random Processes, and Estimation Theory for Engineers", Journal of the American Statistical Association, Jan. 1994, Jun. 6, 2014, 10 pages.
Stone, S. S. et al., "Accelerating advanced MRI reconstructions on GPUs", J. Parallel Distrib. Comput. 68 (2008) 1307-1318, www.elsevier.com/locate/jpdc, Jun. 28, 2008, 12 pages.
Sutton, Bradley P. et al., "Fast, Iterative Image Reconstruction for MRI in the Presence of Field Inhomogeneities", IEEE Transactions on Medical Imaging, vol. 22, No. 2, Feb. 2003, Feb. 2003, 11 pages.
Toledo, Jon B. et al., "Contribution of cerebrovascular disease in autopsy confirmed neurodegenerative disease cases in the National Alzheimer's Coordinating Centre", Brain 2013: 136; 2697-2706, Jul. 10, 2013, 10 pages.
Walsh, David O. et al., "Adaptive Reconstruction of Phased Array MR Imagery", Magnetic Resonance in Medicine 43:682-690 (2000), 2000, 9 pages.
Warmuth, Carsten et al., "Quantification of Blood Flow in Brain Tumors: Comparison of Arterial Spin Labeling and Dynamic Susceptibilityweighted Contrast-enhanced MR Imaging", Radiology 2003; 228:523-532, 2003, 10 pages.
Wetscherek, Andreas et al., "Flow-Compensated Intravoxel Incoherent Motion Diffusion Imaging", Magnetic Resonance in Medicine 74:410-419 (2015), Aug. 12, 2014, 10 pages.
Wu, Xiao-Long et al., "Magnetic Resonance in Medicine 43:682-690 (2000)", 2011 IEEE; ISBI 2011, http://impact.crhc.illinois.edu/mri.php, 2011, 4 pages.
Wurnig, Mortiz C. et al., "Systematic Analysis of the Intravoxel Incoherent Motion Threshold Separating Perfusion and Diffusion Effects: Proposal of a Standardized Algorithm", Magnetic Resonance in Medicine 74:1414-1422 (2015), 2015, 9 pages.
Zhang, Qinwei et al., "Cramer-Rao Bound for Intravoxel Incoherent Motion Diffusion Weighted Imaging Fitting", 35th Annual International Conference of the IEEE EMBS; Osaka, Japan, Jul. 3-7, 2013, Jul. 2013, 4 pages.
Zhang, Yongyue et al., "Segmentation of Brain MR Images Through a Hidden Markov Random Field Model and the Expectation-Maximization Algorithm", IEEE Transactions on Medical Imaging, vol. 20, No. 1, Jan. 2001, Jan. 2001, 13 pages.
Bernstein, Matt A. et al., "Handbook of MRI Pulse Sequences", Elsevier Academic Press, 2004, 1041 pages.
Cerjanic, et al., "Using IVIM and diffusion weighted MRI to measure vascular properties in the aging brain", CRCNS 2015 Poster (printed across 2 pages), Presented Sep. 28, 2015 through Sep. 30, 2015, Sep. 28, 2015, 2 pgs.
Eggmont, PPN et al., "Maximum Penalized Likelihood Estimation", Springer Series in Statistics, 2001, 580 pgs.
Fournet, Gabrielle et al., "A two-pool model to describe the IVIM cerebral perfusion", Journal of Cerebral Blood Flow & Metabolism 2017, vol. 37(8) 2987-3000, e-published on Jan. 1, 2016, 14 pgs.
Holtrop, et al., "Diffusion Weighted Imaging Using Multi-shot Spiral with a Simultaneous Multi-slice Excitation", 2015, 1 page.
Holtrop, J. et al., "Diffusion Weighted Imaging with Whole Brain Coverage and Sub-Microliter Voxels", Proceedings of the ISMRM 2013:2064, Apr. 20, 2013, 1 pg.
Preussmann, et al., "SENSE: Sensitivity Encoding for Fast MRI", Magnetic Resonance in Medicine 42:952-962 (1999), 1999, 11 pgs.
Rajan, J. et al., "Noise Measurement from Magnitude MRI using Local Estimates of Variance and Skewness", Physics in Medicine and Biology 21;55(16):441-449, 2001. http://dx.doi.org/10.1088/0031-9155/55/22/6973, 2010, 11 pgs.

* cited by examiner

410

430

Obtaining, by a system including a processor, first magnetic resonance imaging (MRI) data of a subject, wherein the first MRI data is obtained during a first scan of the subject, wherein the first scan has a first diffusion sampling time, and wherein the first diffusion sampling time is selected in order to facilitate use of the first MRI data to determine a first Intravoxel Incoherent Motion (IVIM) effective diffusion coefficient in a Stationary Random Flow (SRF) regime
602

Obtaining, by the system, second MRI data of the subject, wherein the second MRI data is obtained during a second scan of the subject, wherein the second scan has a second diffusion sampling time, wherein the second diffusion sampling time is longer than the first diffusion sampling time, and wherein the second diffusion sampling time is selected in order to facilitate use of the second MRI data to determine a second IVIM effective diffusion coefficient in a pseudodiffusion regime
604

Determining, by the system, a blood velocity value based upon the first MRI data
606

Determining, by the system, a segment length value based upon the second MRI data and the blood velocity
608

Calculating a mean blood velocity value based upon a first IVIM effective diffusion coefficient in a Stationary Random Flow (SRF) regime, wherein first the IVIM effective diffusion coefficient in the SRF regime is determined using first magnetic resonance imaging (MRI) data of a subject, wherein the first MRI data is obtained during a first brain scan of the subject, wherein the first brain scan has a first diffusion sampling time, and wherein the first diffusion sampling time is selected to be sufficiently short so as to enable determination of the first IVIM effective diffusion coefficient in the SRF regime using the first MRI data
702

Calculating a mean segment length value based upon a second IVIM effective diffusion coefficient in a pseudodiffusion regime, wherein the second IVIM effective diffusion coefficient in the pseudodiffusion regime is determined using second MRI data of the subject, wherein the second MRI data is obtained during a second brain scan of the subject, wherein the second brain scan has a second diffusion sampling time, wherein the second diffusion sampling time is longer than the first diffusion sampling time, and wherein the second diffusion sampling time is selected to be sufficiently long so as to enable determination of the second IVIM effective diffusion coefficient in the pseudodiffusion regime using the second MRI data
704

MEASURING BLOOD VESSEL CHARACTERISTICS WITH MRI

CROSS-REFERENCE TO RELATED APPLICATION(S)

The present application claims the benefit of priority to U.S. Provisional Application No. 62/516,958, filed on Jun. 8, 2017, which is hereby incorporated by reference in its entirety.

STATEMENT AS TO FEDERALLY SPONSORED RESEARCH

This invention was made with government support under R01EB018107 and F30AG055283 awarded by the National Institutes of Health. The government has certain rights in this invention.

FIELD OF THE DISCLOSURE

The subject disclosure relates generally to measuring blood vessel characteristics with magnetic resonance imaging (MRI), and more specifically to measuring blood vessel characteristics with multiple diffusion-weighted MRI acquisitions.

BACKGROUND

The worldwide cost of dementia and related disorders had been estimated at $818 billion in 2015 with costs expected to reach $2 trillion by 2030. Over 500,000 deaths were attributable to Alzheimer's disease (AD) alone in 2010. While the cost of Alzheimer's disease and other dementias are clear, both in financial and human terms, developing effective treatments has in effect remained out of reach. It is believed that this is likely due to a combination of failure to understand key steps in the pathogenesis of dementia as well as a lack of mechanisms to measure the emergence of pathobiological changes in the early stages of dementia through noninvasive biomarkers.

To understand the changes in the microvascular architecture that accompany AD, investigators have traditionally relied on sophisticated histological and immunohistological methods to laboriously document changes in post-mortem samples in selected regions of the brain (as shown in FIGS. 1A and 1B—see Baloyannis S J, Baloyannis I S. The vascular factor in Alzheimer's disease: a study in Golgi technique and electron microscopy. J Neurol Sci. 2012; 322(1-2):117-21). These histological techniques, while capable of visualizing the degradation of the microvasculature in great detail, one microscope field at a time, fundamentally lack the ability to be incorporated in prospective longitudinal studies tracking individuals at risk of developing AD or other forms of dementia or to incorporate information about functional measures of blood flow.

BRIEF DESCRIPTION OF THE DRAWINGS

Reference will now be made to the accompanying drawings, which are not necessarily drawn to scale, and wherein:

FIG. 6 depicts an illustrative method according to an embodiment;

FIG. 7 depicts an illustrative method according to an embodiment;

DETAILED DESCRIPTION

Figure 1A:
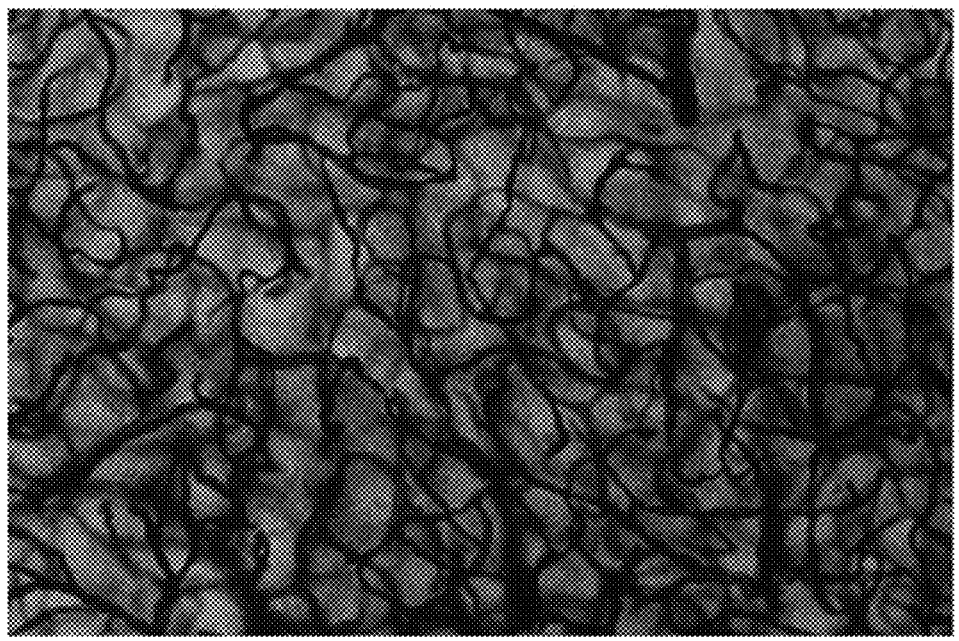
FIG. 1A depicts the CA1 area of hippocampus with capillaries stained from a 72-year old healthy woman.
Figure 1B:
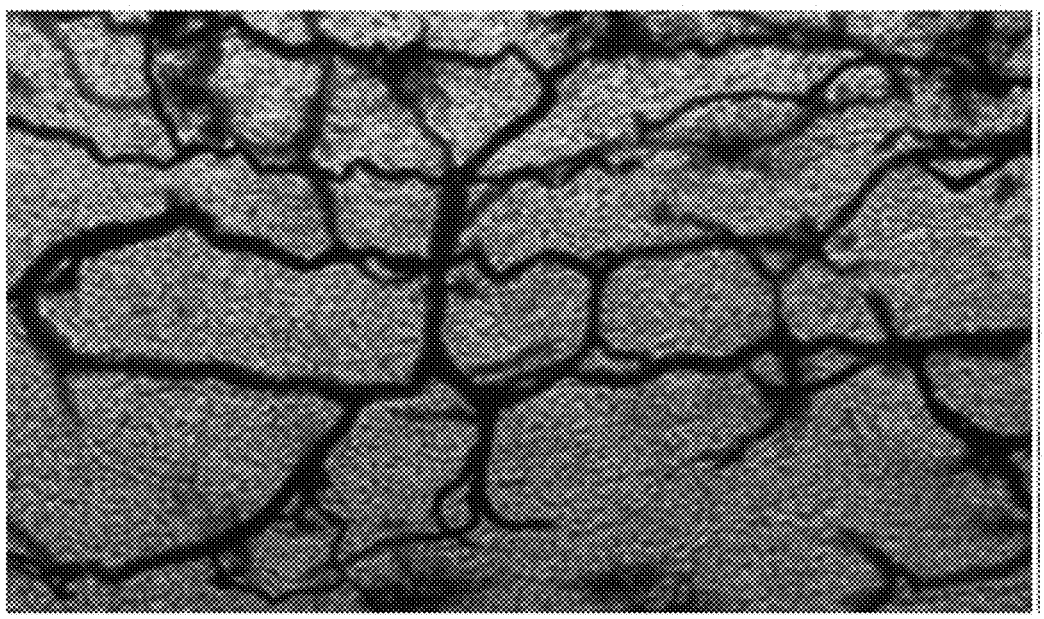
FIG. 1B depicts the CA1 area of hippocampus with stained capillaries in man who suffered from AD. Note the marked decrease of capillary density and increased length of capillaries from branch point to branch point. Tortuosity of the capillary segments is also increased.

One embodiment of the subject disclosure describes a method, comprising: obtaining, by a system including a processor, first magnetic resonance imaging (MRI) data of a subject, wherein the first MRI data is obtained during a first scan of the subject, wherein the first scan has a first diffusion sampling time, and wherein the first diffusion sampling time is selected in order to facilitate use of the first MRI data to determine a first Intravoxel Incoherent Motion (IVIM) effective diffusion coefficient in a Stationary Random Flow (SRF) regime; obtaining, by the system, second MRI data of the subject, wherein the second MRI data is obtained during a second scan of the subject, wherein the second scan has a second diffusion sampling time, wherein the second diffusion sampling time is longer than the first diffusion sampling time, and wherein the second diffusion sampling time is selected in order to facilitate use of the second MRI data to determine a second IVIM effective diffusion coefficient in a pseudodiffusion regime; determining, by the system, a blood velocity value based upon the first MRI data; and determining, by the system, a segment length value based upon the second MRI data.

Another embodiment of the subject disclosure describes a device, comprising: a processing system including a processor; and a memory that stores executable instructions that, when executed by the processing system, perform operations, the operations comprising: calculating a mean blood velocity value based upon a first Intravoxel Incoherent Motion (IVIM) effective diffusion coefficient in a Stationary Random Flow (SRF) regime, wherein the first IVIM effective diffusion coefficient in the SRF regime is determined using first magnetic resonance imaging (MRI) data of a subject, wherein the first MRI data is obtained during a first brain scan of the subject, wherein the first brain scan has a first diffusion sampling time, and wherein the first diffusion sampling time is selected to be sufficiently short so as to enable determination of the first IVIM effective diffusion coefficient in the SRF regime using the first MRI data; and calculating a mean segment length value based upon a second IVIM effective diffusion coefficient in a pseudodiffusion regime, wherein the second IVIM effective diffusion coefficient in the pseudodiffusion regime is determined using second MRI data of the subject, wherein the second MRI data is obtained during a second brain scan of the subject, wherein the second brain scan has a second diffusion sampling time, wherein the second diffusion sampling time is longer than the first diffusion sampling time, and wherein the second diffusion sampling time is selected to be sufficiently long so as to enable determination of the second IVIM effective diffusion coefficient in the pseudodiffusion regime using the second MRI data.

Yet another embodiment of the subject disclosure describes a computer-readable storage medium comprising executable instructions that, when executed by a processing system including a processor, facilitate performance of operations, the operations comprising: acquiring first magnetic resonance imaging (MRI) data of a subject, wherein the first MRI data is acquired during a first scan of the subject, and wherein the first scan has a first diffusion sampling time; generating, based upon the first MRI data, a first plurality of images; determining, based upon the first plurality of images, a first Intravoxel Incoherent Motion (IVIM) effective diffusion coefficient in a Stationary Random Flow (SRF) regime, wherein the first diffusion sampling time is sufficiently short to enable determination of the first IVIM effective diffusion coefficient in the SRF regime; acquiring second MRI data of the subject, wherein the second MRI data is acquired during a second scan of the subject, wherein the second scan has a second diffusion sampling time, and wherein the second diffusion sampling time is longer than the first diffusion sampling time; generating, based upon the second MRI data, a second plurality of images; determining, based upon the second plurality of images, a second IVIM effective diffusion coefficient in a pseudodiffusion regime, wherein the second diffusion sampling time is sufficiently long to enable determination of the second IVIM effective diffusion coefficient in the pseudodiffusion regime; calculating a blood velocity value based upon the first IVIM effective diffusion coefficient in the SRF regime; and calculating a segment length value based upon the second IVIM effective diffusion coefficient in the pseudodiffusion regime.

Various embodiments provide for using biomedical computation to derive noninvasive, quantitative biomarkers from magnetic resonance (MR) data reflecting the underlying state of the microvascular architecture. Through diffusion-weighted MR imaging, the microvascular network can be probed by the use of pulse sequences with radically different diffusion sampling times. By accurately quantifying the observed motion of capillary blood, the microvascular architecture in a voxel can be summarized into quantitative biomarkers. With the noninvasive, neuroimaging-based biomarkers of various embodiments described herein, investigators will be able to measure longitudinal changes in the brain microvasculature, nondestructively, giving investigators the ability to link microvascular structure with cognitive function and disease progression not currently possible with post-mortem histology.

Reference will now be made to certain embodiments with respect to diffusion MRI for the measurement of noninvasive microvascular biomarkers. By measuring the average motion of blood, diffusion MRI presents the opportunity to target measurements to microvascular blood flow (unlike arterial spin labeling (ASL) which does not measure microvascular blood dynamics but overall perfusion and delivery). While hypoperfusion is an important factor in the course of AD and other forms of dementia, the temporal relationship between the onset of regional hypoperfusion and microvascular degradation is not yet apparent. Techniques such as ASL and positron emission tomography (PET), can report perfusion via cerebral blood flow (CBF) but not the blood dynamics such as capillary length or capillary blood velocity. Separating differences between reported degeneration of the overall density of microvessels or dysregulation of microvascular flow requires a method (as described herein according to various embodiments) with differential sensitivity to CBF and to the motions of the blood as it moves through the microvasculature.

As described herein in connection with various embodiments, diffusion MRI presents the opportunity to define biomarkers of structure, such as mean capillary length in terms of observed function, by measuring the dynamic motion of blood. Furthermore, due to the rapid decay of the pseudodiffusion signal from large vessels, measurements of only microvascular blood flow and diffusion can be made (while it is possible for ASL to separate the arterial phases from the microvascular and capillary phases of CBF based on post-labeling delay, the cerebral transit time in healthy aged controls and dementia patients may vary depending on disease status, possibly making the reported CBF dependent on the choice of post-labeling delay and disease status).

Reference will now be made to certain embodiments with respect to Intravoxel Incoherent Motion (IVIM), which is a biophysically rich model with usefulness that can be leveraged through computation. Le Bihan's IVIM model dates back more than 30 years to the beginning of diffusion weighted imaging in humans. While the original insights led to the field of diffusion weighted imaging, including diffusion tensor imaging and tractography, the ability of IVIM to differentiate microvascular perfusion and diffusion signals through model fitting was quickly identified as a significant opportunity for diffusion MRI.

The classical IVIM model uses a two compartment model for the microvascular blood flow as shown in Equation 1:

$$S=S_0[f\exp(-bD^*)+(1-f)\exp(-bD)].$$

The parameter, f, reflects the microvascular blood signal, or perfusion, fraction, while D and D* represent the diffusion and IVIM-specific effective diffusion coefficients. D* reflects the microvascular blood flow by capturing the diffusion-like microscopic blood motions according to the Einstein relation for diffusion as shown in Table 1, below.

TABLE 1

Summary of relationships between IVIM effective diffusion coefficients and the Einstein relation.

| | Passive (True) Diffusion | Stationary Random Flow regime | Pseudodiffusion regime |
|---|---|---|---|
| (Pseudo) Diffusion coefficient | $D = \dfrac{E[l^2]}{6\Delta t}$ | $D^*_{SRF} = \dfrac{\overline{v}^2 t_{diff}}{6}$ | $D^*_{pseudo} = \dfrac{\overline{v}l}{6}$ |

TABLE 1-continued

Summary of relationships between IVIM effective diffusion coefficients and the Einstein relation.

| | Passive (True) Diffusion | Stationary Random Flow regime | Pseudodiffusion regime |
|---|---|---|---|
| Required Condition | Only Brownian motion present | $\bar{v} t_{diff} < \bar{l}$ | $t_{diff} > 10 \frac{\bar{l}}{\bar{v}}$ |

At its heart, the Einstein relation shows the dependence of the effective diffusion coefficient, D*, on the mean square displacement, l, and the diffusion time, Δt. As used herein, the passive (true) diffusion coefficient is denoted using Δt., rather than t_diff to emphasize that the measured diffusion coefficient in the true diffusion case does not depend on the diffusion sampling time, t_diff. For the other cases, the measured D* parameters will depend on the t_diff employed by the pulse sequence. For the condition where the diffusion sampling time is long enough for the blood to transit through a sufficient number of capillaries (typically understood to be a number greater than 3-5), the use of the pseudodiffusion model is shown to be accurate. On the contrary, for diffusion sampling times so short that the spins in blood do not have time to completely transit a single capillary segment on average, Callaghan proposed a Stationary Random Flow (SRF) model describing the ballistic trajectory of the blood as shown in Table 1. These two models provide a biophysical basis for the use (as described herein in connection with various embodiments) of mean microvascular blood velocity (MBV), $\bar{v}$, and mean microvascular segment length (MSL), $\bar{l}$, as biomarkers for microvascular health in the brain (since their effect on the diffusion weighted MR signal can be predicted and measured). As blood travels only within vessels in the brain, the average straight line segment length of blood motion measured via IVIM directly reflects the average straight line segment length of the vessel that the blood is traveling in.

While the IVIM model, encompassing the SRF and pseudodiffusion regimes have existed for at least 20 years, the use of diffusion weighted images with radically different diffusion sampling times to estimate microvascular parameters (as described herein in connection with various embodiments) is believed to have not been attempted. This gap in the literature may be due to the technological challenges of obtaining diffusion sampling times in excess of 400 ms (as used in various embodiments) and the relative recent development of gradients strong enough (as used in various embodiments) to obtain the short diffusion sampling time required to apply the IVIM model in the SRF regime.

Reference will now be made to certain embodiments directed to a reliable and robust IVIM estimator. In this regard, IVIM parameter estimates have typically been difficult to obtain reliably, especially in the brain on clinical scanners. This difficulty is due (at least in part) to the very large SNR (signal to noise ratio) required for reliable D* estimates as predicted by the Cramer-Rao lower bound. By correctly modeling (as provided by various embodiments) the Rician noise present in DW-MR (diffusion weighted magnetic resonance) data as part of the estimation process for Rician noise, the estimation of IVIM parameters can be improved according to various embodiments in two ways. First, as the IVIM model only applies to magnitude DWI (diffusion-weighted imaging) data, the assumption of Gaussian noise is effectively never satisfied, as the nonlinear magnitude operation transforms complex Gaussian noise to real Rician noise. While it has typically been thought in the field that for SNR values above 3 the Rician noise can be assumed to be Gaussian, for IVIM this assumption is incorrect. Even with very high quality diffusion MR data, assuming a typical perfusion fraction of 5% in the brain and an SNR of 20 in the lowest b-value image, the SNR of the passive diffusion compartment is 19. However, the SNR of the critical compartment, the signal arising from blood flow in microvasculature, has an effective SNR of only 1. The second way that IVIM estimation can be improved according to an embodiment is through the use of a biased estimator, such as a maximum likelihood based method with the assumption of Rican noise, which can perform better than the Cramer-Rao Lower Bound in accordance with estimation theory.

Figure 2:
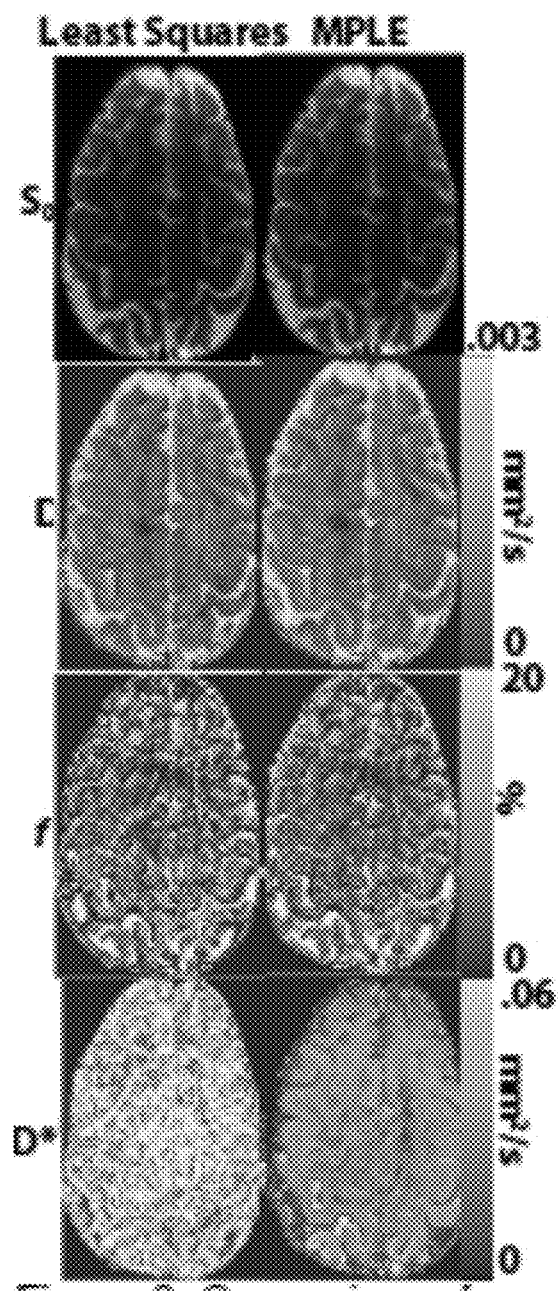
FIG. 2 depicts a comparison of images associated with a standard least squares estimator (left column) for Intravoxel Incoherent Motion parameters and a maximum penalized likelihood estimator (MPLE) according to an embodiment (right column) at high resolution (1.04 mm in-plane, 1.25 mm through plane)

In various embodiments, to apply the IVIM model to diffusion MR image data of typical clinical quality, a maximum penalized likelihood estimator (MPLE) has been developed and applied to the estimation of IVIM parameters from diffusion MR images. Preliminary results show that the estimation of D*, the pseudodiffusion coefficient, is strongly affected by the choice of estimator scheme, between the MPLE and the Gaussian noise-assuming least squares estimator (see FIG. 2—showing comparison of images associated with a standard least squares estimator (left column) for IVIM parameters and an embodiment of an MPLE estimator (right column) at high resolution (1.04 mm in-plane, 1.25 mm through plane)). The MPLE based estimator of this embodiment, combined with SNR efficient advanced diffusion acquisition, shows improved visualization of D* parameters maps across a slice of the brain at much higher resolution (1.04 mm×1.04 mm×1.25 mm) than is typically achievable with IVIM acquisition protocols. Certain conventional fitting methods typically fit the diffusion coefficient first, selecting a b-value above which it is assumed there is no signal from the pseudodiffusion. The choice of b-value at which to partition the data can strongly influence the estimated parameters as shown in the literature in the liver. The MPLE of an embodiment uses all of the diffusion weighted data to fit the data simultaneously without such a priori assumptions.

The use of the MPLE of an embodiment as described herein requires the use of a local optimizer, such as the KNITRO or fmincon (MATLAB) estimator, which will provide only a local minimum of the cost function. To find the optimal fit, convexity is required, which is not necessarily true for the MPLE cost function. The use of biophysically relevant initialization parameters is one strategy to ensure that the optimizer will converge to the biophysically accurate optimum. Recent literature has used Monte Carlo Markov Chain (MCMC) estimation in the framework of a data driven Bayesian estimation scheme by using assumptions of spatial homogeneity and strong assumptions of prior probability distributions of the IVIM parameters. An alternative approach is the use of MCMC optimization using independent Metropolis sampling (MCMC-IMS). The MCMC approach is a global optimizer allowing the use of the same cost function as used in the MPLE according to an embodiment, but is unaffected by non-convexity. The MCMC approach is also highly parallelizeable across multiple voxels via OpenACC and GPU acceleration, presenting an option for increasing scale to take advantage of future biomedical computing resources.

Reference will now be made to a discussion (according to various embodiments) of sensitivity of quantitative biomarkers to reflect microvascular blood flow from multiple time scales and to thus reflect architecture changes in aging and AD.

Various microvascular changes with aging have been reported: reduced capillary density, reduced capillary length density (total capillary length per unit volume), and increased tortuosity (defined as the ratio of total capillary length to straight line distance between branch points). Subjects with AD have shown increases in capillary length density rather than decreases in capillary length density, likely due to loss of neuron cell density in AD. Tortuosity, such as that caused by coiling and looping of microvessels, can increase in AD to a larger extent than with normal aging.

Microvascular architecture parameters are traditionally measured from histological stains using alkaline phosphatase or endothelial markers. As histology is destructive, functional blood flow cannot be observed by this conventional mechanism when classifying or measuring the architectural properties of the microvasculature. However, properties of the microvasculature are only interesting in certain regards as they relate to brain function and health, specifically the ability of the microvasculature to support neurons with oxygen, nutrients, and remove waste products, including toxic byproducts of metabolism like β-amyloid (Aβ) in AD. While perfusion can be measured with ASL, this ASL mechanism is typically unable to differentiate the reasons for hypoperfusion, such as vascular dysregulation or microvascular degeneration.

In various embodiments, relevant, quantitative biomarkers for microvascular function can be isolated from the IVIM model and the diffusion MR signal by observing the motion of blood perfusing the brain. Specifically, various embodiments can be used to quantify microvascular perfusion fraction (MPF), microvascular segment length (MSL), and microvascular blood velocity (MBV). In various embodiments, these measures can be combined and compared with those from standard techniques, like ASL.

Figure 3:
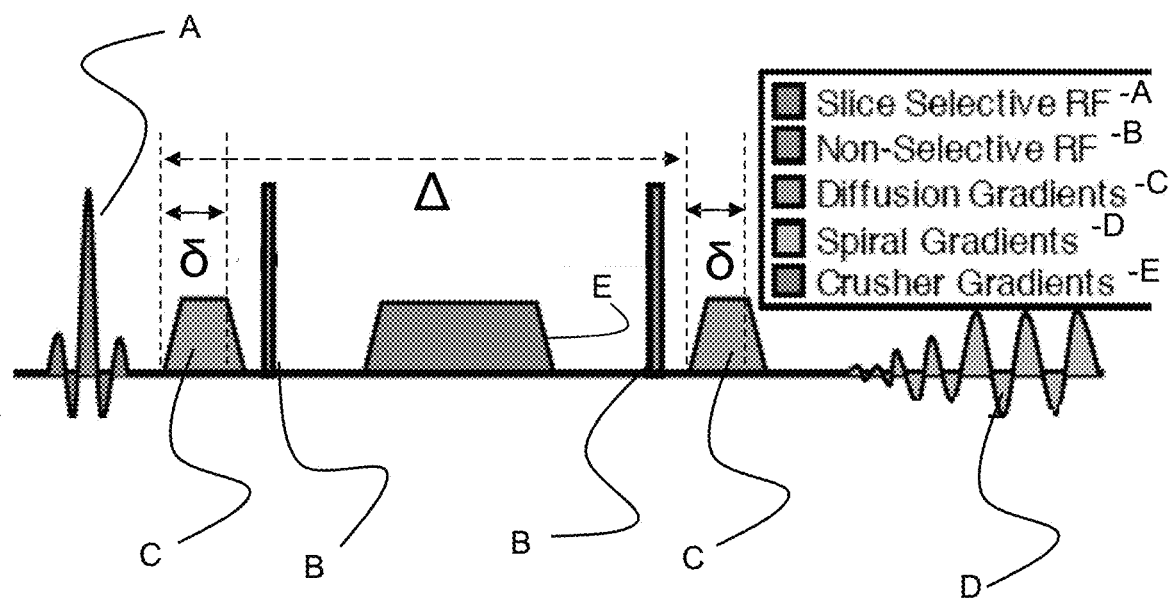
FIG. 3 depicts a condensed diagram showing an illustrative embodiment of a stimulated echo acquisition mode pulse sequence 302 as implemented on a SIEMENS TRIO scanner.
Figure 10:
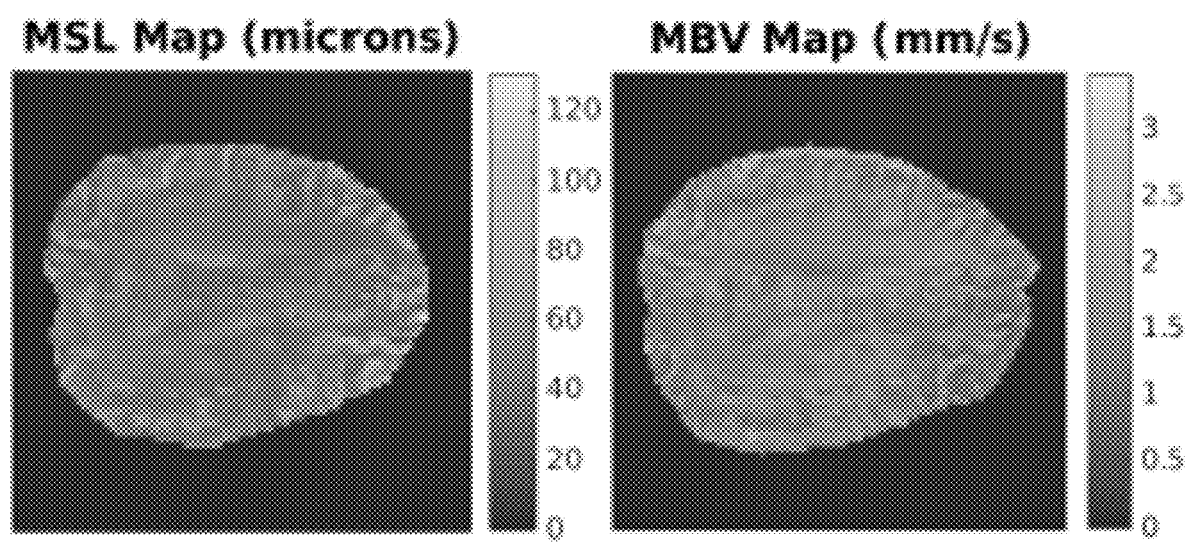
FIG. 10 depicts microvascular segment length for a young subject in a slice high in the brain (left) and microvascular blood velocity for the same subject on the same slice (right)—resolution: 2 mm isotropic, scan time is 24:00 minutes total for both required scans.

One embodiment described herein implements a stimulated echo acquisition mode (STEAM) diffusion sequence modified with a novel, hybrid scheme with slice selective and nonselective RF pulses and a 3 part phase cycling scheme. The diffusion encoding in this embodiment is applied to an SNR efficient spiral readout capable of high resolution on clinical scanners. By combining nonselective pulses for the refocusing 90° pulses, eliminating diffusion weighting from the slice selection gradients, combined with phase cycling for free induction decay signal suppression, the minimum b-value obtainable in this embodiment is cut from approximately 25 s/mm² to 12 s/mm². Sampling adequate low b-values is essential to obtaining accurate parameter estimates when using the IVIM model. FIG. 3 shows this embodiment of the STEAM diffusion encoding with the hybrid slice selective and nonselective RF pulse scheme used (one unique aspect of the embodiments described herein relates to the two non-selective refocusing RF pulses used to generate the stimulated echo). As seen in FIG. 3, the slice selective RF pulse is shown by the letter "A", the two non-selective RF pulses are shown by the letter "B", the two diffusion gradients are shown by the letter "C", the spiral gradients are shown by the letter "D" and the crusher gradients are shown by the letter "E". As seen in this FIG., Δ is defined here as occurring from the beginning of the first diffusion gradient to the beginning of the second diffusion gradient. Likewise, δ is defined as occurring from the beginning of each diffusion gradient to the end of the flattop time of the trapezoidal waveform. Both Δ and δ are used to calculate and define the diffusion sampling time via the relationship $t\_diff = \Delta + \delta$ for the STEAM sequence shown. Other diffusion pulse sequences can have different relationships between the timing parameters and the diffusion sampling times achieved. In the case of STEAM, the diffusion sampling time can be quite long, $\Delta = 400$ ms used in this example, while $\delta = 6$ ms, through the use of a stimulated echo at a cost of half of the pulsed gradient spin echo (PGSE)-equivalent SNR. The STEAM sampling parameters used in this example are TE/TR=45 ms/2000 ms with an FA=90°. The PGSE sequence (in this example, TE/TR=75/2000 ms, and flip angle=90°) is limited by T2 decay to a diffusion sampling time of $t_{diff}$=23.3 ms. Taken together, the PGSE and STEAM sequences, two different D* parameters can be obtained. Using the relationships shown in Table 2 (below), MBV ($\bar{v}$) can be quantified on a voxel by voxel basis from the PGSE data, and then MSL ($\bar{l}$) can be quantified by using the D* from the STEAM data and the MBV. A preliminary result of MBV ($\bar{v}$) and MSL ($\bar{l}$) quantified in a young male healthy volunteer (mid-20s) is shown in FIG. 10. The coefficient of variation for MSL ($\bar{l}$) is relatively low at 0.2571, which can be incorporated in a power analysis. The MSL averaged across gray and white matter for the slice shown is 45.7 μm which compares well to a mean microvessel segment length of 59.4 μm in a post-mortem histology based analysis of human gray matter. The MBV of 1.44 mm/s falls within the range of red blood cell velocities observed in rats.

TABLE 2

Calculating MBV and MSL from diffusion coefficient relationships from Table 1.

| PGSE (Short Diffusion Time) | STEAM (Long Diffusion Time) |
| --- | --- |
| $\bar{v} = \sqrt{\dfrac{6D^*_{PGSE}}{t_{diff}}}$ | $\bar{l} = \dfrac{6D^*_{STEAM}}{\bar{v}}$ |

Figure 4A:
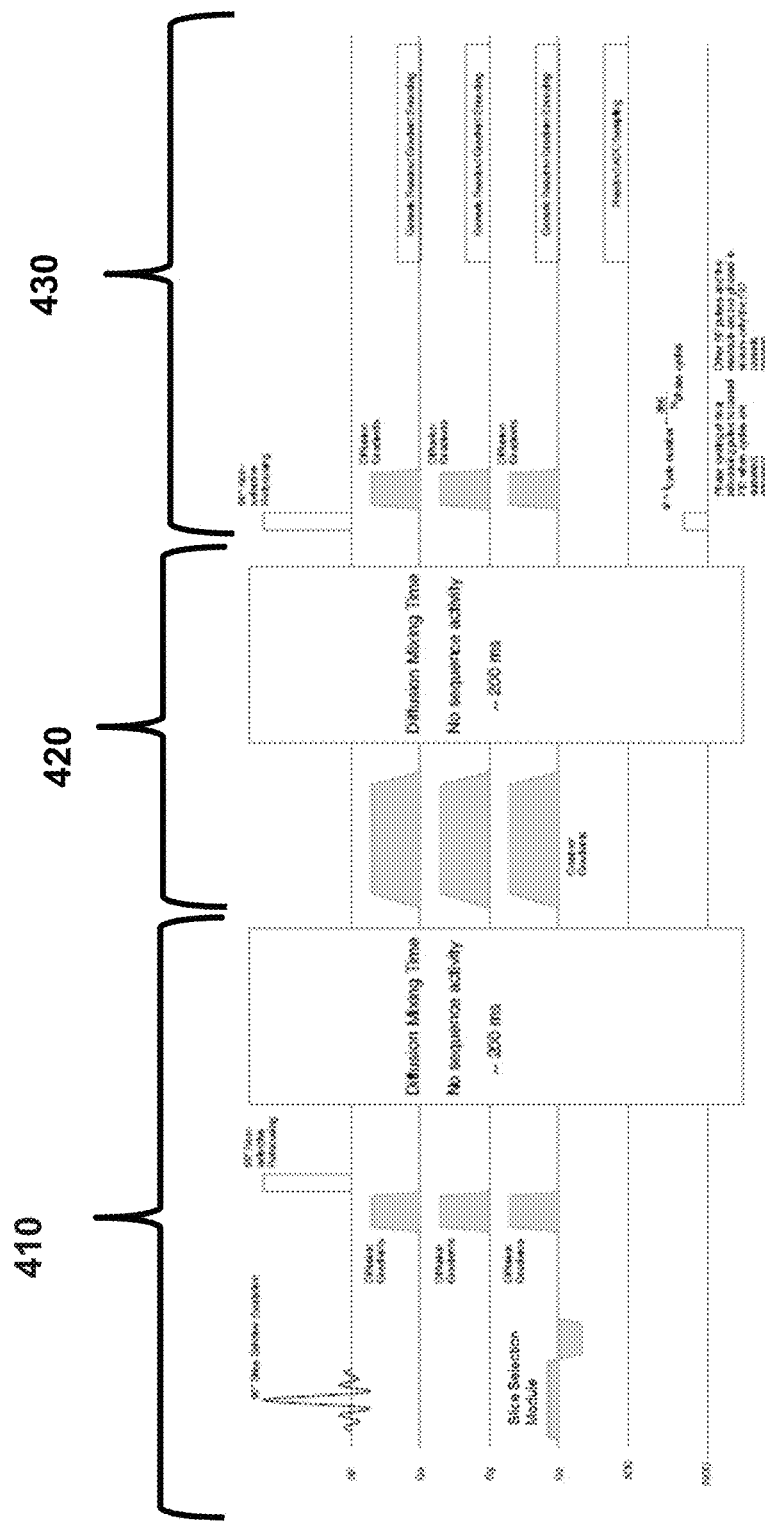
FIG. 4A depicts a diagram showing another embodiment of a stimulated echo acquisition mode pulse sequence 402.

Referring now to FIG. 4A, this depicts a diagram showing another embodiment of a stimulated echo acquisition mode (STEAM) pulse sequence 402. As seen in this FIG. 4A, the line marked "RF" includes a 90° slice selective excitation, a 90° non-selective refocusing and a diffusion mixing time (see also FIG. 4B, showing detail of the section of FIG. 4A marked "410"), and another diffusion mixing time (see also FIG. 4C, showing detail of the section of FIG. 4A marked "420") and another 90° non-selective refocusing (see also FIG. 4D, showing detail of the section of FIG. 4A marked "430").

Figure 4B:
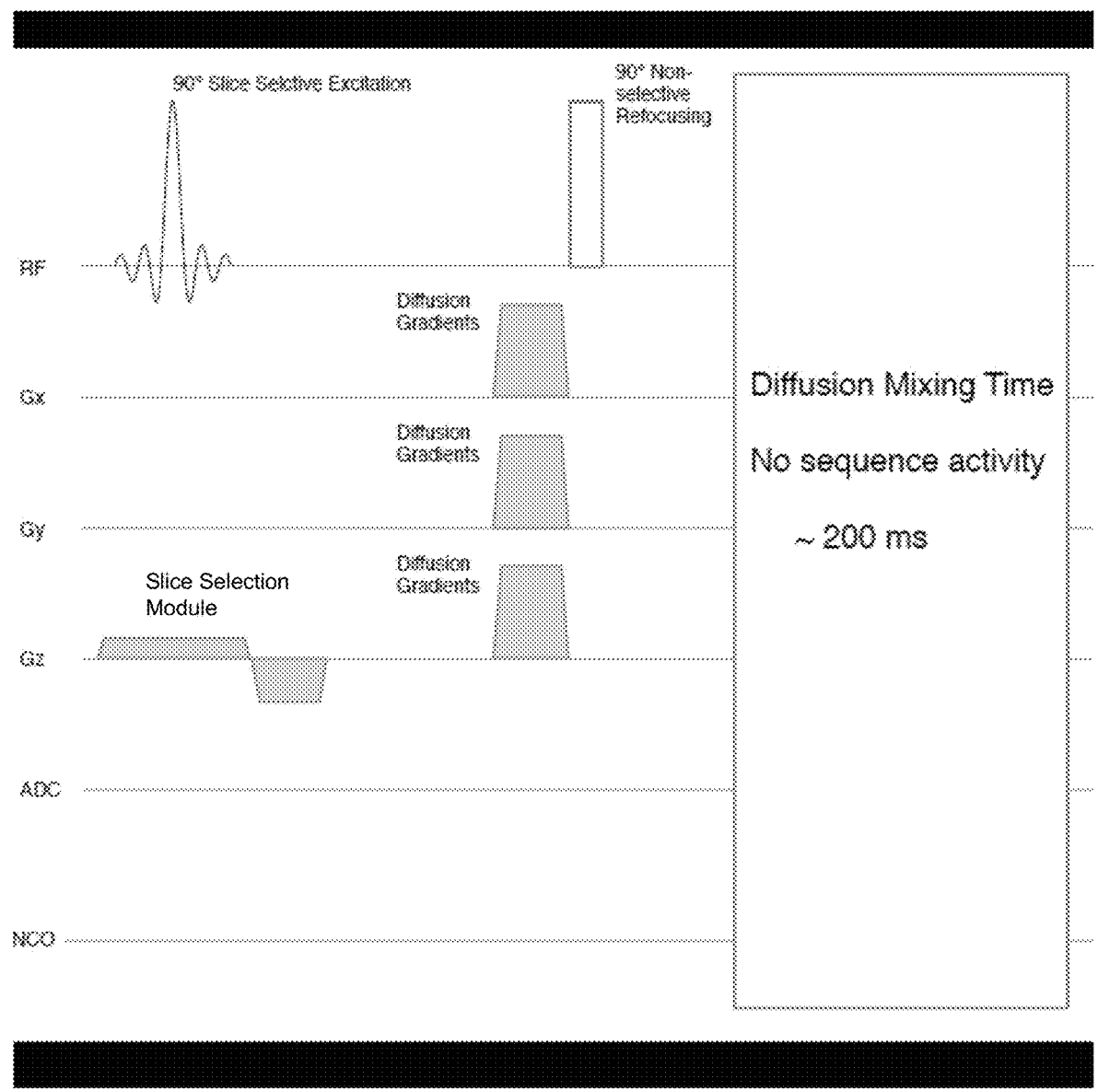
FIGS. 4B, 4C and 4D depict details of certain portions of FIG. 4A.
Figure 4C:
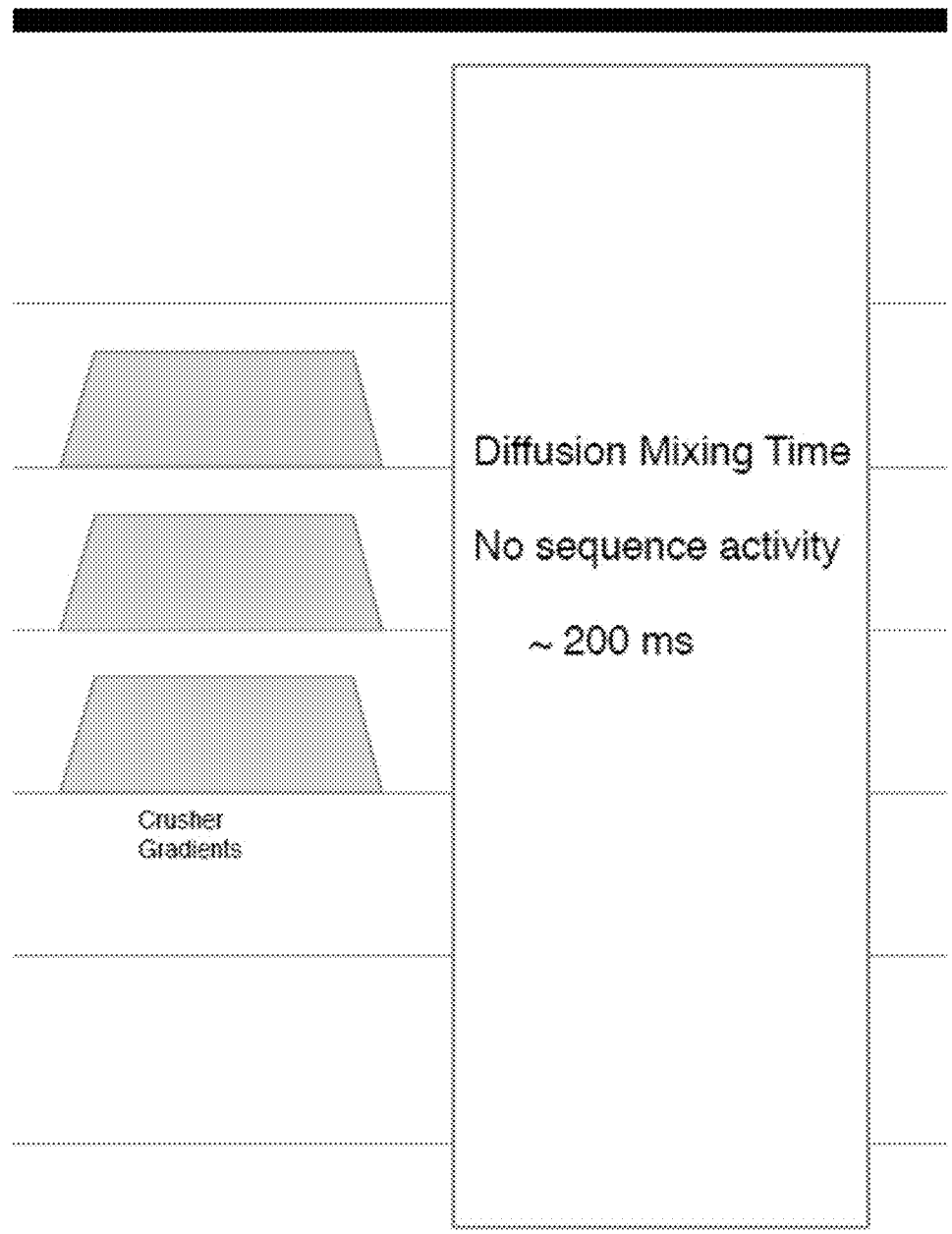
Figure 4D:
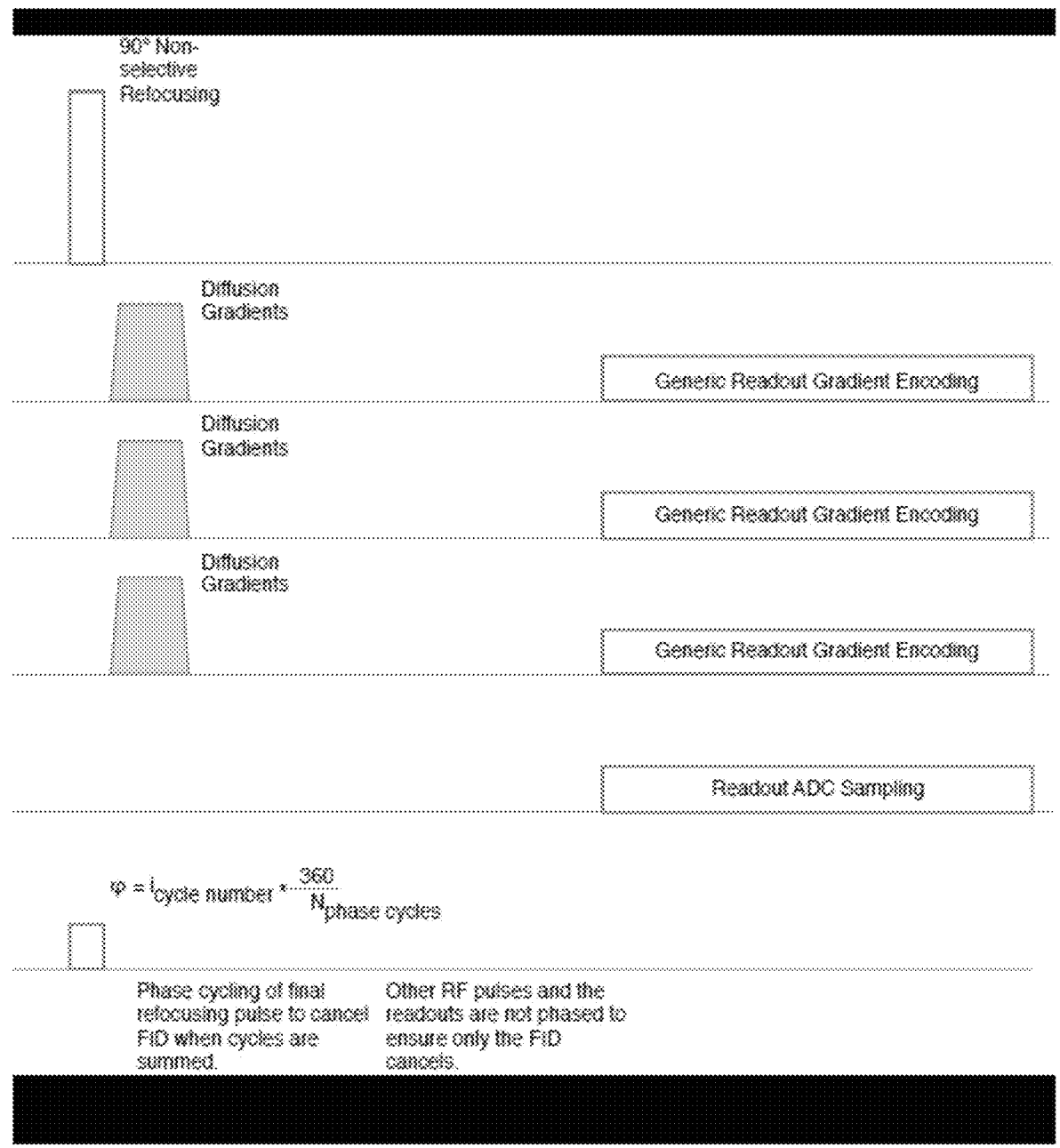

Still referring to FIG. 4A, the line marked "Gx" includes diffusion gradients and diffusion mixing time (see also FIG. 4B, showing detail of the section of FIG. 4A marked "410"), a crusher gradient and another diffusion mixing time (see also FIG. 4C, showing detail of the section of FIG. 4A marked "420") and diffusion gradients and generic readout gradient encoding (see also FIG. 4D, showing detail of the section of FIG. 4A marked "430").

Still referring to FIG. 4A, the line marked "Gy" includes diffusion gradients and diffusion mixing time (see also FIG. 4B, showing detail of the section of FIG. 4A marked "410"), a crusher gradient and another diffusion mixing time (see also FIG. 4C, showing detail of the section of FIG. 4A marked "420") and diffusion gradients and generic readout gradient encoding (see also FIG. 4D, showing detail of the section of FIG. 4A marked "430").

Still referring to FIG. 4A, the line marked "Gz" includes a Slice Selection Module (consisting of a slice selection gradient and a slice select rewinder gradient), diffusion gradients and diffusion mixing time (see also FIG. 4B, showing detail of the section of FIG. 4A marked "410"), a crusher gradient and another diffusion mixing time (see also FIG. 4C, showing detail of the section of FIG. 4A marked "420") and diffusion gradients and generic readout gradient encoding (see also FIG. 4D, showing detail of the section of FIG. 4A marked "430").

Still referring to FIG. 4A, the line marked "ADC" includes diffusion mixing time (see also FIG. 4B, showing detail of the section of FIG. 4A marked "410"), another diffusion mixing time (see also FIG. 4C, showing detail of the section of FIG. 4A marked "420") and readout ADC sampling (see also FIG. 4D, showing detail of the section of FIG. 4A marked "430").

Still referring to FIG. 4A, the line marked "NCO" (numerically controlled oscillator) includes diffusion mixing time (see also FIG. 4B, showing detail of the section of FIG. 4A marked "410"), another diffusion mixing time (see also FIG. 4C, showing detail of the section of FIG. 4A marked "420") and phase cycling (see also FIG. 4D, showing detail of the section of FIG. 4A marked "430").

In one specific example, the diffusion mixing times of FIGS. 4A, 4B and 4C can involve no sequence activity and can be approximately 200 ms. In another specific example, the phase cycling of the final refocusing pulse can be used to cancel FID (Free Induction Decay) when cycles are summed. In another specific example, other RF pulses and the readouts are not phased to ensure only the FID cancels. In another specific example related to the phase cycling:

$$\varphi = i_{cycle\ number} \times \frac{360}{N_{phase\ cycles}}.$$

Figure 5:
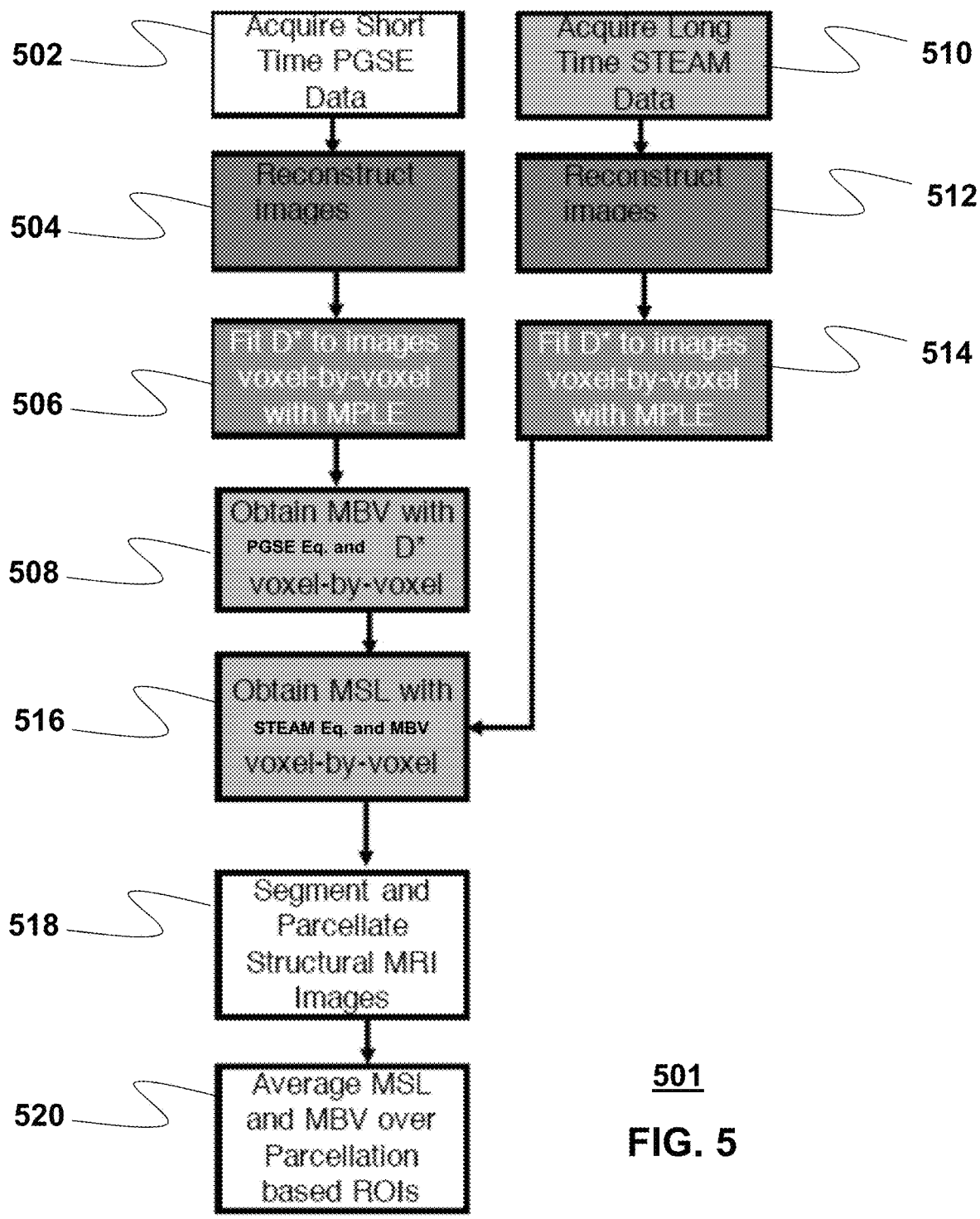
FIG. 5 depicts an illustrative method according to an embodiment.

Referring now to FIG. 5, this depicts an illustrative embodiment of a method 501 (used to quantify microvascular biomarkers using PGSE data and STEAM data) in accordance with various aspects described herein. As seen in this FIG. 5, step 502 is to acquire short time PGSE data, step 504 is to reconstruct images (from the PGSE data) with PowerGrid, and step 506 is to fit D* to the images (from step 504). The fitting of D* (associated with the PGSE) in step 506 can be carried out voxel-by-voxel with an MPLE process (such as described herein). In addition, step 508 is to obtain MBV ($\bar{v}$). This step 508 can be accomplished using the PGSE (Short Diffusion Time) equation from Table 2 and D* from step 506 voxel-by-voxel. Still referring to FIG. 5, step 510 is to acquire long time STEAM data, step 512 is to reconstruct images (from the STEAM data) with PowerGrid, and step 514 is to fit D* to the images (from step 512). The fitting of D* (associated with the STEAM data) in step 514 can be carried out voxel-by-voxel with an MPLE process (such as described herein). In addition, step 516 is to obtain MSL (l) This step 516 can be accomplished using the STEAM (Long Diffusion Time) equation from Table 2 and D* from step 514 voxel-by-voxel. Still referring to FIG. 5, step 518 is to segment and parcellate structural MRI images and step 520 is to average MSL and MBV over parcellation based on ROIs (regions of interest).

While for purposes of simplicity of explanation, the respective processes are shown and described as a series of blocks in FIG. 5, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

As described herein, relevant biomarkers can be determined via use of two different data sets. In one specific example, a first data set can be obtained via use of a first pulse sequence (PGSE) and a second (different) data set can be obtained via use of a second (different) pulse sequence (STEAM).

Referring now to FIG. 6, this depicts an illustrative embodiment of a method 601 in accordance with various aspects described herein. As seen in this FIG. 6, step 602 comprises obtaining, by a system including a processor, first magnetic resonance imaging (MRI) data of a subject, wherein the first MRI data is obtained during a first scan of the subject, wherein the first scan has a first diffusion sampling time, and wherein the first diffusion sampling time is selected in order to facilitate use of the first MRI data to determine a first Intravoxel Incoherent Motion (IVIM) effective diffusion coefficient in a Stationary Random Flow (SRF) regime. Next, step 604 comprises obtaining, by the system, second MRI data of the subject, wherein the second MRI data is obtained during a second scan of the subject, wherein the second scan has a second diffusion sampling time, wherein the second diffusion sampling time is longer than the first diffusion sampling time, and wherein the second diffusion sampling time is selected in order to facilitate use of the second MRI data to determine a second IVIM effective diffusion coefficient in a pseudodiffusion regime. Next, step 606 comprises determining, by the system, a blood velocity value based upon the first MRI data. Next, step 608 comprises determining, by the system, a segment length value based upon the second MRI data and the blood velocity (which had been determined in step 606). In one example, the blood velocity is an estimated blood velocity. In another example, the segment length value is an estimated segment length value.

While for purposes of simplicity of explanation, the respective processes are shown and described as a series of blocks in FIG. 6, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

In one example, the first scan is a first brain scan and the second scan is a second brain scan.

In another example, the method further comprises: determining, by the system, the first IVIM effective diffusion coefficient in the SRF regime using a PGSE pulse sequence; and determining, by the system, the second IVIM effective diffusion coefficient in the pseudodiffusion regime using a long diffusion mixing time STEAM diffusion weighted pulse sequence.

In another example: the determining the first IVIM effective diffusion coefficient in the SRF regime comprises determining the first IVIM effective diffusion coefficient in the SRF regime by fitting to first images associated with the first MRI data (this being the short diffusion sampling time data); and the determining the second IVIM effective diffusion coefficient in the pseudodiffusion regime comprises determining the second IVIM effective diffusion coefficient in the pseudodiffsive regime by fitting to second images associated with the second MRI data (this being the data from the long time STEAM sequence).

In another example: the fitting to the first images comprises first fitting with an MPLE; and the fitting to the second images comprises second fitting with the MPLE.

In another example: the first fitting is on a first voxel-by-voxel basis in association with the first images; and the second fitting is on a second voxel-by-voxel basis in association with the second images.

In another example: the determining the blood velocity value based upon the first MRI data comprises determining the blood velocity value based upon the first IVIM effective diffusion coefficient in the SRF regime; and the determining the segment length value based upon the second MRI data comprises determining the segment length value based upon the second IVIM effective diffusion coefficient in the pseudodiffusion regime.

In another example: the blood velocity value is a mean value; and the determining the blood velocity value based upon the first IVIM effective diffusion coefficient in the SRF regime is performed using the formula:

$$\bar{v} = \sqrt{\frac{6D^*_{PGSE}}{t_{diff}}}$$

where $D^*_{PGSE}$ is the first IVIM effective diffusion coefficient in the SRF regime and $t_{diff}$ is the first diffusion sampling time.

In another example: the segment length value is a mean value; and the determining the segment length value based upon the second IVIM effective diffusion coefficient in the pseudodiffusion regime is performed using the formula:

$$\bar{l} = \frac{6D^*_{STEAM}}{\bar{v}}$$

where $D^*_{STEAM}$ is the second IVIM effective diffusion coefficient in the pseudodiffusion regime.

In another example: the first diffusion sampling time is in a range of 10-30 ms (e.g., for a brain scan); and the second diffusion sampling time is in a range of 200-500 ms (e.g., for a brain scan). In various examples, each of the first diffusion sampling time and the second diffusion sampling time can be selected based upon what organ of the subject is being scanned. The first diffusion sampling time is minimized to ensure operation in the SRF regime while accurately sampling the first IVIM effective diffusion coefficient in the SRF regime. The second diffusion sampling time should be selected such that t_diff is greater than 3-5 $\bar{l}/\bar{v}$ for the ranges of MSL and MBV to be characterized.

In another example: the first MRI data is obtained using a scanner; and the second MRI data is obtained using the scanner.

In another example, the scanner is a clinical scanner.

In another example: the first scan of the subject comprises a pulsed gradient spin echo (PGSE) sequence; the second scan of the subject comprises a stimulated echo acquisition mode (STEAM) sequence; and the STEAM sequence comprises a 90° slice selective excitation pulse followed by a first 90° non-selective refocusing pulse and a second 90° non-selective refocusing pulse.

In another example, the STEAM sequence further comprises a plurality of diffusion gradients and none of the 90° slice selective excitation pulse, the first 90° non-selective refocusing pulse, or the second 90° non-selective refocusing pulse overlap in time with any of the diffusion gradients.

Referring now to FIG. 7, this depicts an illustrative embodiment of a method 701 in accordance with various aspects described herein. As seen in this FIG. 7, step 702 comprises calculating a mean blood velocity value based upon a first IVIM effective diffusion coefficient in a Stationary Random Flow (SRF) regime, wherein first the IVIM effective diffusion coefficient in the SRF regime is determined using first magnetic resonance imaging (MRI) data of a subject, wherein the first MRI data is obtained during a first brain scan of the subject, wherein the first brain scan has a first diffusion sampling time, and wherein the first diffusion sampling time is selected to be sufficiently short so as to enable determination of the first IVIM effective diffusion coefficient in the SRF regime using the first MRI data. Next, step 704 comprises calculating a mean segment length value based upon a second IVIM effective diffusion coefficient in a pseudodiffusion regime, wherein the second IVIM effective diffusion coefficient in the pseudodiffusion regime is determined using second MRI data of the subject, wherein the second MRI data is obtained during a second brain scan of the subject, wherein the second brain scan has a second diffusion sampling time, wherein the second diffusion sampling time is longer than the first diffusion sampling time, and wherein the second diffusion sampling time is selected to be sufficiently long so as to enable determination of the second IVIM effective diffusion coefficient in the pseudodiffusion regime using the second MRI data.

While for purposes of simplicity of explanation, the respective processes are shown and described as a series of blocks in FIG. 7, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

In one example, the operations further comprise: determining the first IVIM effective diffusion coefficient in the SRF regime by fitting to first images associated with the first MRI data; and determining the second IVIM effective diffusion coefficient in the pseudodiffusion regime by fitting to second images associated with the second MRI data.

In another example: the fitting to the first images comprises first fitting with an MPLE, wherein the first fitting is on a first voxel-by-voxel basis in association with the first images; and the fitting to the second images comprises second fitting with the MPLE, wherein the second fitting is on a second voxel-by-voxel basis in association with the second images.

In another example, each of the first MRI data and the second MRI data is obtained using a clinical scanner.

Figure 8:
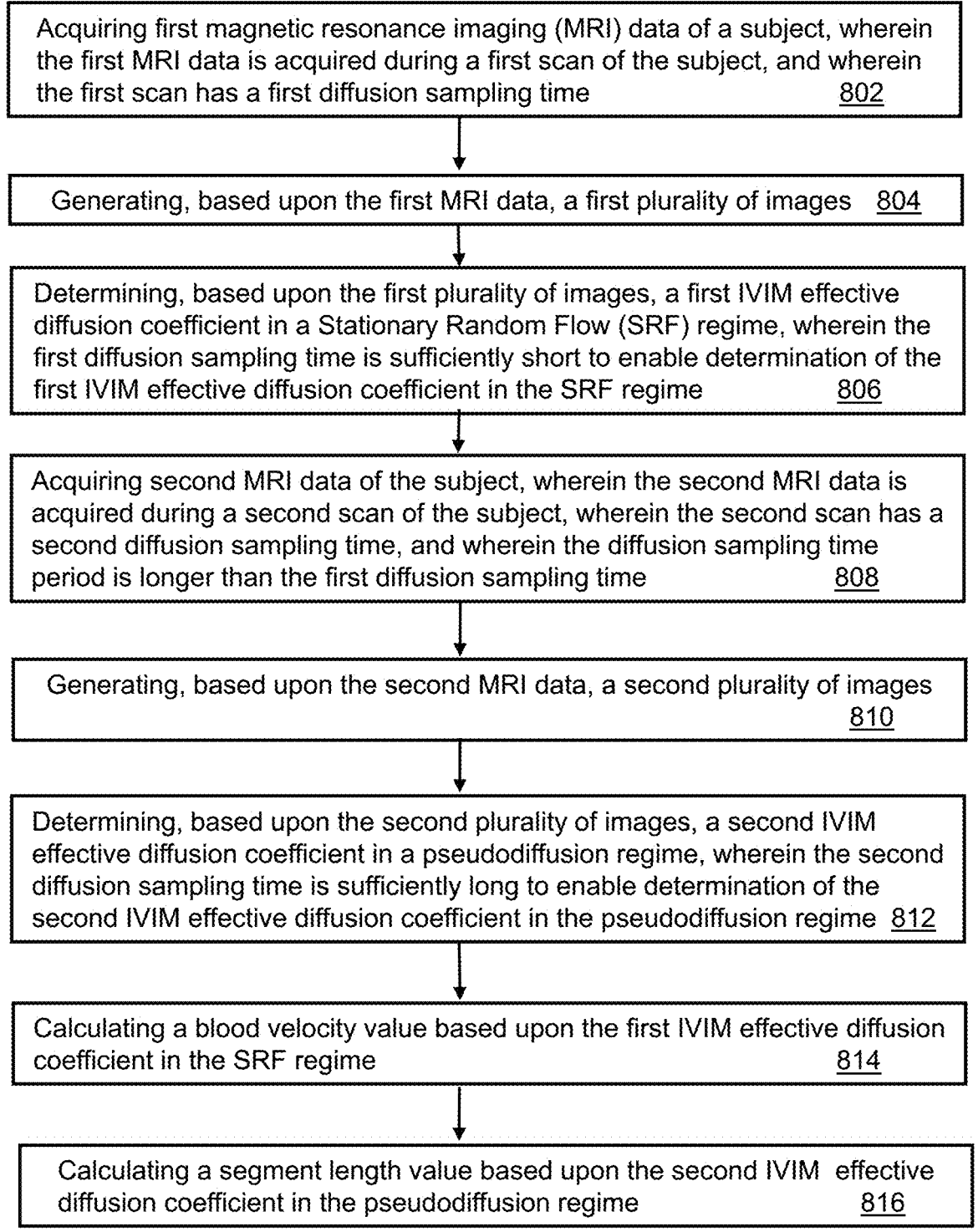
FIG. 8 depicts an illustrative method according to an embodiment.

Referring now to FIG. 8, this depicts an illustrative embodiment of a method 801 in accordance with various aspects described herein. As seen in this FIG. 8, step 802 comprises acquiring first magnetic resonance imaging (MRI) data of a subject, wherein the first MRI data is acquired during a first scan of the subject, and wherein the first scan has a first diffusion sampling time. Next, step 804 comprises generating, based upon the first MRI data, a first plurality of images. Next, step 806 comprises determining, based upon the first plurality of images, a first IVIM effective diffusion coefficient in a Stationary Random Flow (SRF) regime, wherein the first diffusion sampling time is sufficiently short to enable determination of the first IVIM effective diffusion coefficient in the SRF regime. Next, step 808 comprises acquiring second MRI data of the subject, wherein the second MRI data is acquired during a second scan of the subject, wherein the second scan has a second diffusion sampling time, and wherein the second diffusion sampling time is longer than the first diffusion sampling time. Next, step 810 comprises generating, based upon the second MRI data, a second plurality of images. Next, step 812 comprises determining, based upon the second plurality of images, a second IVIM effective diffusion coefficient in a pseudodiffusion regime, wherein the second diffusion sampling time is sufficiently long to enable determination of the second IVIM effective diffusion coefficient in the pseudodiffusion regime. Next, step 814 comprises calculating a blood velocity value based upon the first IVIM effective diffusion coefficient in the SRF regime. Next, step 816 comprises calculating a segment length value based upon the second IVIM effective diffusion coefficient in the pseudodiffusion regime.

While for purposes of simplicity of explanation, the respective processes are shown and described as a series of blocks in FIG. 8, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

In one example: the first IVIM effective diffusion coefficient in the SRF regime is determined by fitting the first IVIM effective diffusion coefficient in the SRF regime to the first plurality of images on a first voxel-by-voxel basis; and wherein the second IVIM effective diffusion coefficient in the pseudodiffusion regime is determined by fitting the second IVIM effective diffusion coefficient in the pseudodiffusion regime to the second plurality of images on a second voxel-by-voxel basis.

In another example: the fitting the first IVIM effective diffusion coefficient in the SRF regime to the first plurality of images on the first voxel-by-voxel basis is performed using a first MPLE process; and the fitting the second IVIM effective diffusion coefficient in the pseudodiffusion regime to the second plurality of images on the second voxel-by-voxel basis is performed using a second MPLE process.

In another example, the first scan is a first brain scan and wherein the second scan is a second brain scan.

Figure 9:
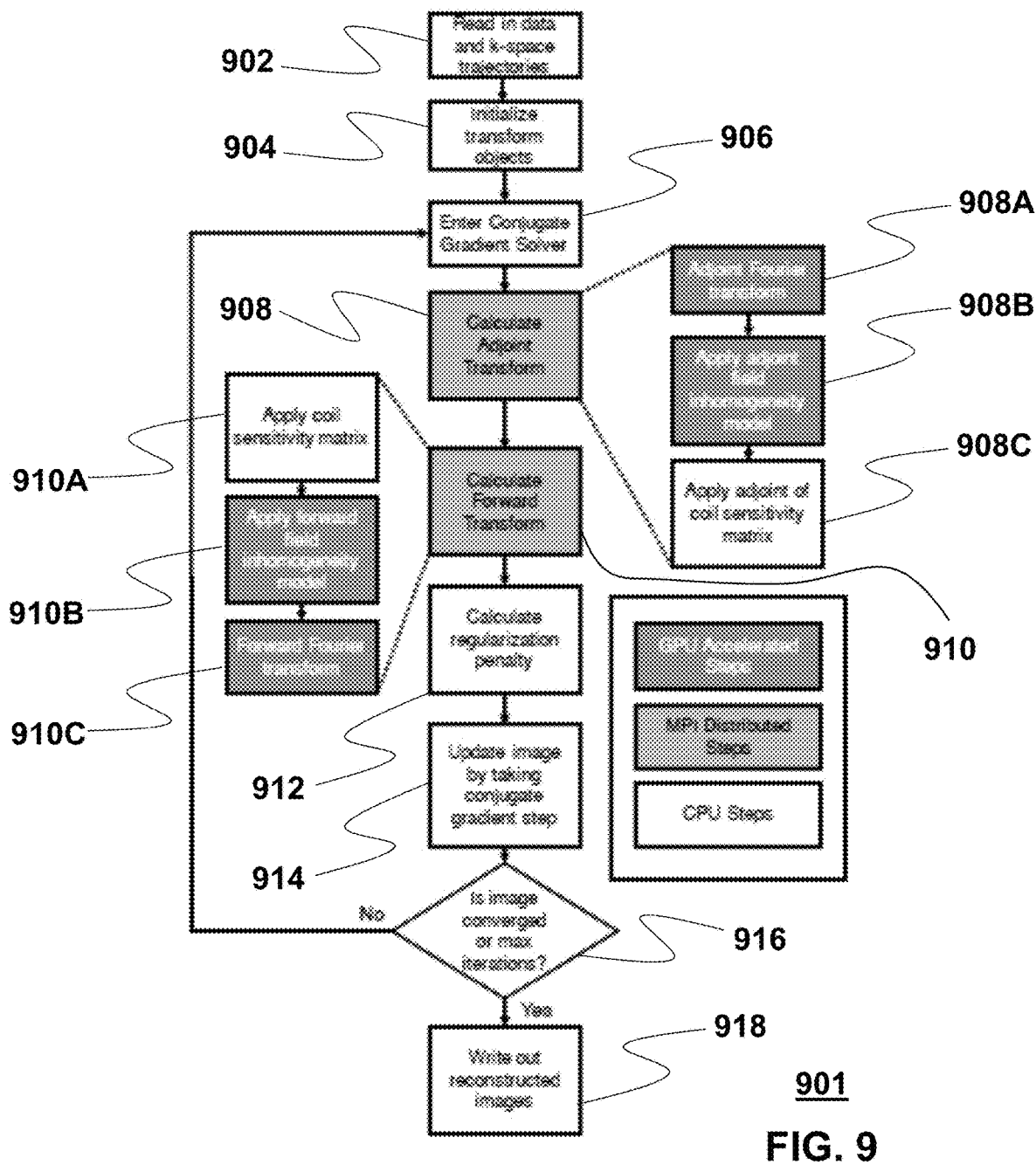
FIG. 9 depicts an illustrative method according to an embodiment.

Referring now to FIG. 9, this depicts an illustrative embodiment of a method 901 in accordance with various aspects described herein. In the below description each step is indicated as being one of: accelerated with OpenACC (GPU accelerated steps); distributed across multiple computers (MPI distributed steps); or CPU steps. As seen in this FIG. 9, step 902 (CPU step) is to read in data and k-space trajectories. Step 904 (CPU step) is to initialize transform objects. Step 906 (CPU step) is to enter conjugate gradient solver. Step 908 (MPI distributed step) comprises steps 908A, 908B and 908C and is to calculate adjoint transform. Step 908A (GPU accelerated step) is adjoint Fourier transform. Step 908B (GPU accelerated step) is apply adjoint field inhomogeneity model. Step 908C (CPU step) is to apply adjoint of coil sensitivity matrix. Step 910 (MPI distributed step) comprises steps 910A, 910B and 910C and is to calculate forward transform. Step 910A (CPU step) is to apply coil sensitivity matrix. Step 910B (GPU accelerated step) is apply forward field inhomogeneity model. Step 910C (GPU accelerated step) is forward Fourier transform. Step 912 (CPU step) is to calculate regularization penalty. Step 914 (CPU step) is to update image by taking conjugate gradient. Step 916 (CPU step) is to determine whether image is converged or maximum iterations reached. If "No", return to step 906. If "Yes", proceed to step 918. Step 918 (CPU step) is to write out reconstructed images.

While for purposes of simplicity of explanation, the respective processes are shown and described as a series of blocks in FIG. 9, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

As described herein (see, e.g., FIG. 9 and the associated text) various embodiments provide a reconstruction workflow as implemented in PowerGrid for an iterative non-Cartesian SENSE (Sensitivity Encoding) image reconstruction.

As described herein (see, e.g., FIG. 9 and the associated text) various embodiments provide a reconstruction workflow including steps in a non-Cartesian SENSE reconstruction using GPU and distributed memory parallelism.

In one specific example (see, e.g., FIG. 9 and the associated text), key steps can be accelerated with GPU processors and distributed MPI code so that many GPUs (e.g., as many as 32) can be applied to accomplish a single image reconstruction quickly (e.g., in 33 s).

As described herein, various embodiments provide mechanisms to measure the emergence of pathobiological changes in the early stages of dementia through noninvasive biomarkers.

As described herein, is an investigation of the role of impaired microvasculature as an etiology in AD and related dementias, such as vascular dementia.

As described herein, various embodiments provide mechanisms to facilitate obtaining a set of new quantitative, effective biomarkers (e.g., in the context of brain microvascular architecture).

As described herein, acquisition elements can be provided in order to create image(s) of brain microvasculature at high resolution and "reasonable" computing time.

As described herein, image reconstruction elements can be provided in order to create image(s) of brain microvasculature at high resolution and "reasonable" computing time.

As described herein, various embodiments can be used to diagnose and/or track Alzheimer's Disease (and/or other neurological disorders).

As described herein, diagnostics mechanisms for neurological disorders are provided (in one specific example, diagnostics can be used to track disease progress and/or effect of therapies).

As described herein, various embodiments provide for high SNR efficiency acquisitions, computational power sufficient to form the high SNR images, and an estimation framework with correct noise model.

As described herein, various embodiments provide for imaging at multiple diffusion time scales to enable examination of microvascular biomarkers related to volume fraction, mean length, and mean velocity.

As described herein are mechanisms to acquire data and use that data to create images of microvasculature in the brain, both geometry and blood flow. In one example, a computational estimation scheme is provided to quantify IVIM model parameters (e.g., perfusion fraction, psuedodiffusion coefficient).

As described herein is a maximum penalized likelihood estimation to enable mapping of IVIM parameters related to blood flow.

As described herein is a pulse sequence. In one example, the pulse sequence includes slice selective RF, non-selective RF, diffusion gradients, spiral gradients, crusher gradients.

As described herein are mechanisms to use data (which can be acquired as described herein) to reconstruct images.

In one example, the mechanisms can use advanced non-Cartesian acquisition coupled with model-based image reconstruction. In another example, the mechanisms can use techniques from HPC (high performance computing).

As described herein, various embodiments can be used to diagnose (or help diagnose) AD while the patient is still alive.

As described herein, various embodiments can provide high-resolution image maps.

As described herein are mechanisms for measuring blood vessel characteristics of suspected Alzheimer patients.

In one embodiment, reliable measures of the microvascular architecture can be made using two diffusion times.

In another embodiment, more than two diffusion times can be used in order to increase the precision of the estimation. In one example, more diffusion times can be incorporated into the scanning protocol at the cost of marginally increased scan time.

Various embodiments of the estimation framework described herein may not allow for the incorporation of additional diffusion sampling time points. Thus, an alternative model that exists in the literature and that uses the velocity autocorrelation function to predict the shape of the diffusion weighted MR signal across multiple diffusion sampling times can be used. This latter model can be adapted to use the estimator mechanisms described herein in connection with various embodiments and/or to use the sequences described herein in connection with various embodiments to combine data from three or more diffusion sampling times.

As described herein, open source parallel image reconstruction software can be used to support quantification of the biomarkers of various embodiments in clinically relevant time frames.

As described herein, various embodiments utilize advanced, non-Cartesian trajectories to obtain the SNR required to characterize the state of the microvasculature in the brain via quantitative biomarkers. Using highly SNR efficient pulse sequences, such as spiral readouts, and advanced, model based reconstructions incorporating field inhomogeneity and image regularization, the performance of 3T clinical scanners can be extended to enable the estimations described herein.

In one specific example, parallelism can be exploited as a path towards accelerating the computationally intensive algorithms, such as the multishot, non-Cartesian, field inhomogeneity and motion-induced-phase corrected reconstructions that can be used. In another specific example, general purpose graphics processing units (GPU), multicore hardware, and parallel computation can be one practical path enabling quantitative microvascular biomarkers via advanced reconstruction algorithms.

As described herein, various embodiments use diffusion MR to measure changes in the microvascular network in the brain.

As described herein, various embodiments can facilitate longitudinal studies of AD augmented with measures of microvascular health in vivo, with a complete package of tools encompassing data acquisition, image reconstruction, and biomarker estimation.

As described herein, various embodiments provide integration with models that enable estimation of average capillary length and average blood velocity.

As described herein, various embodiments provide mechanisms via which IVIM D* coefficients can be obtained.

As described herein, various embodiments provide an extra long STEAM sequence.

From the descriptions herein, it would be evident to an artisan with ordinary skill in the art that the various embodiments can be modified, reduced, or enhanced without departing from the scope and spirit of the claims described below. For example, information from any desired number of scans (e.g., brain scans) can be combined, analyzed and/or visualized (e.g., as images on a computer screen, as printed images) as described herein. Other suitable modifications can be applied to the subject disclosure. Accordingly, the reader is directed to the claims for a fuller understanding of the breadth and scope of the subject disclosure.

Figure 11:
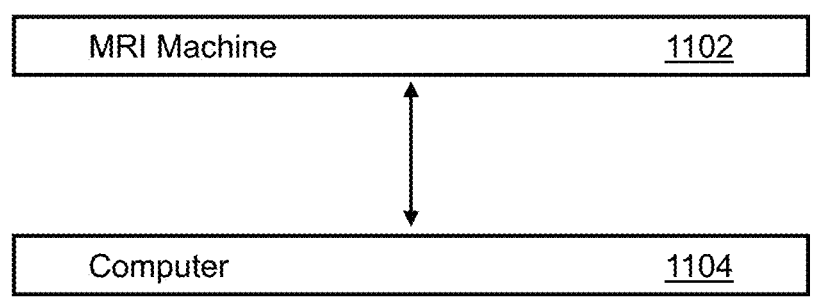
FIG. 11 depicts an illustrative diagrammatic representation of a system according an embodiment.

Referring now to FIG. 11, this depicts an illustrative diagrammatic representation of a system 1101 according to an embodiment. As seen in this FIG. 11, system 1101 includes MRI machine 1102 in operative communication with computer 1104. The MRI machine 1102 can obtain MRI data from a patient (not shown) and can be controlled by and/or provide data to the computer 1104. In one specific example, one or more pulse sequences (such as described herein) can be implemented in MRI machine 1102 and/or computer 1104 by software (and/or by software in combination with firmware/hardware). In one specific example, the MRI machine (which can be referred to as a scanner) comprises several elements: a magnet (usually a superconducting solenoidal magnet) that provides a static magnetic field, as well as gradient coils used to introduce time-varying and spatially-varying magnetic fields. Nuclear Magnetic Resonance active nuclei, such as $^1$H, located in the magnetic field of the main magnet, can be excited by the use of Radio Frequency (RF) transmitters in concert with resonant coils, such as a body coil. These excited nuclei are manipulated via magnetic field gradients induced by the gradient coils and associated hardware to encode imaging data in the nuclear magnetic resonance signals emitted by the object being imaged and sampled by RF receiver hardware in concert with resonant coils. The coordination of RF transmit pulses, magnetic field gradients, and RF receiver sampling are all coordinated by computer systems running a specific program that implements a scheme, called a pulse sequence, to image the object. Once the data is received from the object, using knowledge of the pulse sequence and the received data, the data is reconstructed using Fourier transforms, and other knowledge about the physics of the MR imaging process to generate human readable images. All of this is coordinated via a human interface, often known as a console or host, where users can visualize the results of scans, and prescribe additional scans, often inputting parameters into the pulse sequences to obtain specific types of images.

Figure 12:
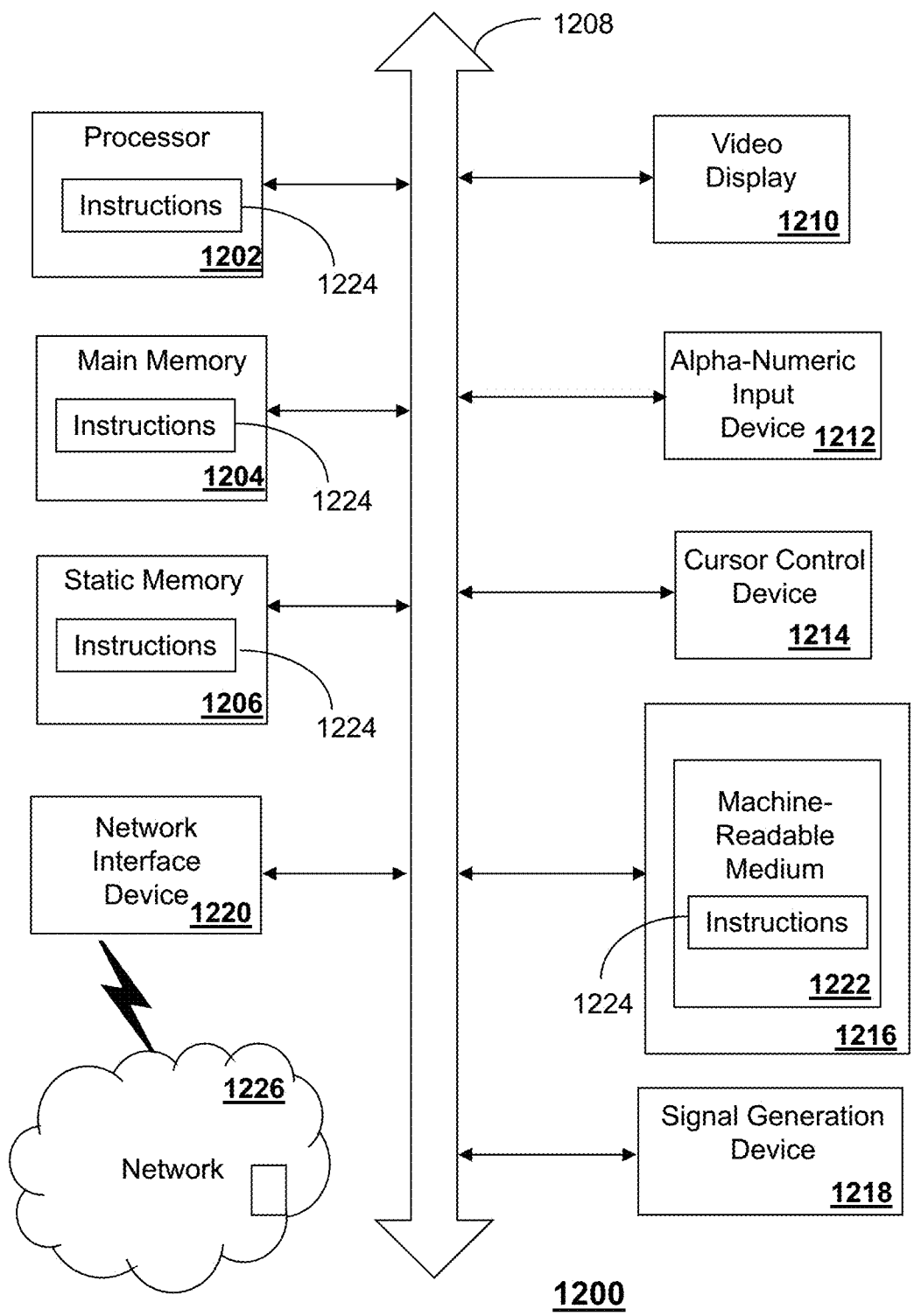
FIG. 12 depicts an illustrative diagrammatic representation of a machine in the form of a computer system within which a set of instructions, when executed, may cause the machine to perform any one or more of the methodologies disclosed herein.

Referring now to FIG. 12, this depicts an exemplary diagrammatic representation of a machine in the form of a computer system 1200 within which a set of instructions, when executed, may cause the machine to perform any one or more of the methods discussed above. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 1200 may include a processor 1202 (e.g., a central processing unit (CPU), a graphics processing unit (GPU, or both), a main memory 1204 and a static memory 1206, which communicate with each other via a bus 1208. The computer system 1200 may further include a video display unit 1210 (e.g., a liquid crystal display (LCD), a flat panel, or a solid state display. The computer system 1200 may include an input device 1212 (e.g., a keyboard), a cursor control device 1214 (e.g., a mouse), a disk drive unit 1216, a signal generation device 1218 (e.g., a speaker or remote control) and a network interface device 1220.

The disk drive unit 1216 may include a tangible computer-readable storage medium 1222 on which is stored one or more sets of instructions (e.g., software 1224) embodying any one or more of the methods or functions described herein, including those methods illustrated above. The instructions 1224 may also reside, completely or at least partially, within the main memory 1204, the static memory 1206, and/or within the processor 1202 during execution thereof by the computer system 1200. The main memory 1204 and the processor 1202 also may constitute tangible computer-readable storage media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

While the tangible computer-readable storage medium 1222 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth, WiFi, Zigbee), and long-range communications (e.g., WiMAX, GSM, CDMA) are contemplated for use by computer system 300.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A method comprising:
    obtaining, by a system including a processor, first magnetic resonance imaging (MRI) data of a subject, wherein the first MRI data is obtained during a first scan of the subject, wherein the first scan has a first diffusion sampling time, and wherein the first diffusion sampling time is selected in order to facilitate use of the first MRI data to determine a first Intravoxel Incoherent Motion (IVIM) effective diffusion coefficient in a Stationary Random Flow (SRF) regime;

determining, by the system, via use of the first MRI data, the first IVIM effective diffusion coefficient in the SRF regime;

obtaining, by the system, second MRI data of the subject, wherein the second MRI data is obtained during a second scan of the subject, wherein the second scan has a second diffusion sampling time, wherein the second diffusion sampling time is longer than the first diffusion sampling time, and wherein the second diffusion sampling time is selected in order to facilitate use of the second MRI data to determine a second IVIM effective diffusion coefficient in a pseudodiffusion regime;

determining, by the system, via use of the second MRI data, the second IVIM effective diffusion coefficient in the pseudodiffusion regime;

determining, by the system, a blood velocity value based upon the first IVIM effective diffusion coefficient in the SRF regime; and determining, by the system, a blood vessel segment length value based upon both the second IVIM effective diffusion coefficient in the pseudodiffusion regime and the blood velocity value.

2. The method of claim 1, wherein the first scan is a first brain scan and wherein the second scan is a second brain scan.

3. The method of claim 1, wherein:
the determining the first IVIM effective diffusion coefficient in the SRF regime comprises determining the first IVIM effective diffusion coefficient in the SRF regime by fitting the first IVIM effective diffusion coefficient to first images associated with the first MRI data; and
the determining the second IVIM effective diffusion coefficient in the pseudodiffusion regime comprises determining the second IVIM effective diffusion coefficient in the pseudodiffusion regime by fitting the second IVIM effective diffusion coefficient to second images associated with the second MRI data.

4. The method of claim 3, wherein:
the fitting to the first images comprises first fitting with a maximum penalized likelihood estimator (MPLE); and
the fitting to the second images comprises second fitting with the MPLE.

5. The method of claim 4, wherein:
the first fitting is on a first voxel-by-voxel basis in association with the first images; and
the second fitting is on a second voxel-by-voxel basis in association with the second images.

6. The method of claim 1, wherein:
the blood velocity value is a first mean value; and
the determining the blood velocity value based upon the first IVIM effective diffusion coefficient in the SRF regime is performed using a formula:

$$\bar{v} = \sqrt{\frac{6D^*_{PGSE}}{t_{diff}}}$$

where $D^*_{PGSE}$ is the first IVIM effective diffusion coefficient in the SRF regime and $t_{diff}$ is the first diffusion sampling time.

7. The method of claim 6, wherein:
the blood vessel segment length value is a second mean value; and
the determining the blood vessel segment length value based upon both the second IVIM effective diffusion coefficient in the pseudodiffusion regime and the blood velocity value is performed using another formula:

$$\bar{l} = \frac{6D^*_{STEAM}}{\bar{v}}$$

where $D^*_{STEAM}$ is the second IVIM effective diffusion coefficient in the pseudodiffusion regime.

8. The method of claim 1, wherein:
the first diffusion sampling time is in a first range of 10-30 ms; and
the second diffusion sampling time is in a second range of 200-500 ms.

9. The method of claim 1, wherein:
the first MRI data is obtained using a clinical scanner; and
the second MRI data is obtained using the clinical scanner.

10. The method of claim 9, wherein:
the first scan of the subject comprises a pulsed gradient spin echo (PGSE) sequence;
the second scan of the subject comprises a stimulated echo acquisition mode (STEAM) sequence; and
the STEAM sequence comprises a 90° slice selective excitation pulse followed by a first 90° non-selective refocusing pulse and a second 90° non-selective refocusing pulse.

11. The method of claim 10, wherein the STEAM sequence further comprises a plurality of diffusion gradients and none of the 90° slice selective excitation pulse, the first 90° non-selective refocusing pulse, or the second 90° non-selective refocusing pulse overlap in time with any of the diffusion gradients.

12. A device comprising:
a processing system including a processor; and
a memory that stores executable instructions that, when executed by the processing system, perform operations, the operations comprising:
obtaining first magnetic resonance imaging (MRI) data of a subject, wherein the first MRI data is obtained during a first brain scan of the subject, wherein the first brain scan has a first diffusion sampling time, and wherein the first diffusion sampling time is selected to be sufficiently short so as to enable determination of a first Intravoxel Incoherent Motion (IVIM) effective diffusion coefficient in a Stationary Random Flow (SRF) regime using the first MRI data;
determining the first IVIM effective diffusion coefficient in the SRF regime using the first MRI data of the subject;
obtaining second MRI data of the subject, wherein the second MRI data is obtained during a second brain scan of the subject, wherein the second brain scan has a second diffusion sampling time, wherein the second diffusion sampling time is longer than the first diffusion sampling time, and wherein the second diffusion sampling time is selected to be sufficiently long so as to enable determination of a second IVIM effective diffusion coefficient in a pseudodiffusion regime using the second MRI data;
determining the second IVIM effective diffusion coefficient in the pseudodiffusion regime using the second MRI data of the subject;

calculating a mean blood velocity value based upon the first IVIM effective diffusion coefficient in the SRF regime; and calculating a mean blood vessel segment length value based upon both the second IVIM effective diffusion coefficient in the pseudodiffusion regime and the mean blood velocity value.

13. The device of claim 12, wherein the operations further comprise:

the determining the first IVIM effective diffusion coefficient in the SRF regime comprises determining the first IVIM effective diffusion coefficient in the SRF regime by fitting the first IVIM effective diffusion coefficient to first images associated with the first MRI data; and the determining the second IVIM effective diffusion coefficient in the pseudodiffusion regime comprises determining the second IVIM effective diffusion coefficient in the pseudodiffusion regime by fitting the second IVIM effective diffusion coefficient to second images associated with the second MRI data.

14. The device of claim 13, wherein:

the fitting to the first images comprises first fitting with a maximum penalized likelihood estimator (MPLE), wherein the first fitting is on a first voxel-by-voxel basis in association with the first images; and the fitting to the second images comprises second fitting with the MPLE, wherein the second fitting is on a second voxel-by-voxel basis in association with the second images.

15. A non-transitory computer-readable storage medium comprising executable instructions that, when executed by a processing system including a processor, facilitate performance of operations, the operations comprising:

acquiring first magnetic resonance imaging (MRI) data of a subject, wherein the first MRI data is acquired during a first scan of the subject, and wherein the first scan has a first diffusion sampling time;

generating, based upon the first MRI data, a first plurality of images;

determining, based upon the first plurality of images, a first Intravoxel Incoherent Motion (IVIM) effective diffusion coefficient in a Stationary Random Flow (SRF) regime, wherein the first diffusion sampling time is sufficiently short to enable determination of the first IVIM effective diffusion coefficient in the SRF regime;

acquiring second MRI data of the subject, wherein the second MRI data is acquired during a second scan of the subject, wherein the second scan has a second diffusion sampling time, and wherein the second diffusion sampling time is longer than the first diffusion sampling time;

generating, based upon the second MRI data, a second plurality of images;

determining, based upon the second plurality of images, a second IVIM effective diffusion coefficient in a pseudodiffusion regime, wherein the second diffusion sampling time is sufficiently long to enable determination of the second IVIM effective diffusion coefficient in the pseudodiffusion regime;

calculating a blood velocity value based upon the first IVIM effective diffusion coefficient in the SRF regime; and calculating a blood vessel segment length value based upon both the second IVIM effective diffusion coefficient in the pseudodiffusion regime and the blood velocity value.

16. The non-transitory computer-readable storage medium of claim 15, wherein:

the first IVIM effective diffusion coefficient in the SRF regime is determined by fitting the first IVIM effective diffusion coefficient in the SRF regime to the first plurality of images on a first voxel-by-voxel basis; and the second IVIM effective diffusion coefficient in the pseudodiffusion regime is determined by fitting the second IVIM effective diffusion coefficient in the pseudodiffusion regime to the second plurality of images on a second voxel-by-voxel basis.

17. The non-transitory computer-readable storage medium of claim 16, wherein:

the fitting the first IVIM effective diffusion coefficient in the SRF regime to the first plurality of images on the first voxel-by-voxel basis is performed using a first maximum penalized likelihood estimator (MPLE) process; and the fitting the second IVIM effective diffusion coefficient in the pseudodiffusion regime to the second plurality of images on the second voxel-by-voxel basis is performed using a second MPLE process.

18. The non-transitory computer-readable storage medium of claim 15, wherein the first scan is a first brain scan and wherein the second scan is a second brain scan.

19. The non-transitory computer-readable storage medium of claim 15, wherein:

the first diffusion sampling time is in a first range of 10-30 ms; and the second diffusion sampling time is in a second range of 200-500 ms.

20. The non-transitory computer-readable storage medium of claim 15, wherein:

the first MRI data is obtained using a clinical scanner; and the second MRI data is obtained using the clinical scanner.

* * * * *